United States Patent
Bae et al.

(10) Patent No.: US 10,413,607 B2
(45) Date of Patent: Sep. 17, 2019

(54) ANTIBODY SPECIFICALLY BINDING TO ERBB3 AND USE THEREOF

(71) Applicant: ISU ABXIS CO., LTD., Gyeonggi-do (KR)

(72) Inventors: Dong Goo Bae, Gyeonggi-do (KR); Mi Young Kim, Seoul (KR); Young Mi Hur, Gyeonggi-do (KR); Mi Rim Hong, Seoul (KR)

(73) Assignee: ISU ABXIS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/563,227

(22) PCT Filed: Nov. 2, 2016

(86) PCT No.: PCT/KR2016/012545
§ 371 (c)(1),
(2) Date: Sep. 29, 2017

(87) PCT Pub. No.: WO2017/099362
PCT Pub. Date: Jun. 15, 2017

(65) Prior Publication Data
US 2018/0085455 A1  Mar. 29, 2018

(30) Foreign Application Priority Data
Dec. 7, 2015 (KR) ................ 10-2015-0173281

(51) Int. Cl.
| | | |
|---|---|---|
| A61K 39/395 | (2006.01) | |
| C07K 16/32 | (2006.01) | |
| C07K 16/28 | (2006.01) | |
| A61K 31/00 | (2006.01) | |
| A61P 35/00 | (2006.01) | |
| A61K 39/00 | (2006.01) | |

(52) U.S. Cl.
CPC ........ *A61K 39/39558* (2013.01); *A61K 31/00* (2013.01); *A61P 35/00* (2018.01); *C07K 16/2863* (2013.01); *C07K 16/32* (2013.01); *A61K 2039/505* (2013.01); *A61K 2039/507* (2013.01); *A61K 2039/545* (2013.01); *C07K 2317/21* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,481,687 B2 | 7/2013 | Vincent et al. |
| 8,691,225 B2 | 4/2014 | Schoeberl et al. |
| 8,791,244 B2 | 7/2014 | Daly et al. |
| 8,927,694 B2 | 1/2015 | McDonagh et al. |
| 9,034,328 B2 | 5/2015 | Takahashi |
| 9,273,143 B2 | 3/2016 | Daly et al. |
| 10,077,317 B2 | 9/2018 | Garner et al. |
| 2012/0328623 A1 | 12/2012 | Takahashi |
| 2013/0084297 A1 | 4/2013 | Daly et al. |
| 2013/0330772 A1 | 12/2013 | Vincent et al. |

FOREIGN PATENT DOCUMENTS

| | | |
|---|---|---|
| EP | 2 544 680 A2 | 1/2013 |
| KR | 10-2010-0014426 A | 2/2010 |
| KR | 1020100014426 A | 2/2010 |
| TW | 201329103 B1 | 7/2013 |
| WO | 2015/048008 A2 | 4/2015 |

OTHER PUBLICATIONS

Curley et al (Molecular Cancer Therapeutics, Aug. 2015, 14:2642-2652).*
Office Action corresponding to Taiwanese Patent Application No. 105140259, dated Sep. 4, 2017, 7 pages.
Aurisicchio et. al. "The promise of anti-ErbB3 monoclonals as 1-22 new cancer therapeutics", Oncotarget, 2012, vol. 3, pp. 744-758.
Office Action dated Feb. 15, 2019 in related foreign RU application No. 2018113269, all pgs. (translation thereof).
Office Action dated Mar. 26, 2019 in related foreign JP application No. 2018-542089.
2012/176779, A1, WO, U.S. Pat. No. 9,034,328.
2568051, C2, RU, U.S. Pat. No. 8,481,687.
022201, B1, EA, U.S. Pat. No. 8,927,694.
2014/530215, A, JP, U.S. Pat. No. 9,273,143.
2013/537546, A, JP, U.S. Pat. No. 10,077,317.
2013/523166, A, JP, U.S. Pat. No. 8,481,687.
2010/518820, A, JP, U.S. Pat. No. 8,691,225.
Aurisicchio, L., "*The promise of anti-ErbB3 monoclonals as new cancer therapeutics*,"Oncotarget, August, vol. 3, No. 8, p. 744-758.
Ma, et al., "*Targeting of ertB3 receptor to overcome resistance in cancer treatment*", Molecular Cancer 2014, 13:105, nine pages.
Poovassery, et al., "*Antibody targeting of HER2/HER3 signaling overcomes heregulin-induced resistance to PI3K inhibition in prostate cancer*," Int. J. Cancer: 137, p. 267-277, 2015.
Jiang, et al., "*Advances in targeting HER3 as an anticancer therapy*," Chemotherapy Research and Practice, vol. 2012, Article ID 817304, 9 pages.
Jiang, et al., "*Combination of anti-HER3 antibody MM-121/SAR256212 and cetuximab inhibits tumor growth in preclinical models of head and neck squamous cell carcinoma (HNSCC)*," Mol Cancer Ther. Jul. 2014; 12(7): p. 1826-1836.
International Search Report and Written Opinion corresponding to PCT/KR2016/012545, dated Feb. 2, 2017, 13 pages.
Korean Office Action corresponding to Korean Application No. 10-2015-0173281, dated Mar. 3, 2017.

(Continued)

*Primary Examiner* — Laura B Goddard
(74) *Attorney, Agent, or Firm* — Kilpatrick Townsend & Stockton

(57) ABSTRACT

An antibody that specifically binds to ErbB3 or an antigen-binding fragment thereof, and use thereof, are provided. The antibody that specifically binds to ErbB3 or an antigen-binding fragment thereof may be effectively used to prevent or treat a disease related to activation or overexpression of ErbB3 protein.

33 Claims, 9 Drawing Sheets
Specification includes a Sequence Listing.

(56) References Cited

OTHER PUBLICATIONS

Gianluca Sala et al, "EV20, a Novel Anti-ErbB-3 Humanized Antibody, Promotes ErbB-3 Down-Regulation and Inhibits Tumor Growth in Vivo", Translational Oncology, (Dec. 1, 2013), vol. 6, No. 6, doi:10.1593/tlo.13475, ISSN 1936-5233, pp. 676-IN9, XP055168432 [I] 1-15 * the whole document *.

Li Zhang et al, "ERBB3/HER2 Signaling Promotes Resistance to EGFR Blockade in Head and Neck and Colorectal Cancer Models", Molecular Cancer Therapeutics, US, (May 5, 2014), vol. 13, No. 5, doi:10.1158/1535-7163.MCT-13/1033, ISSN 1535-7163, pp. 1345-1355, XP055582372 [I] 1-15 * the whole document *.

Nadege Gaborit et al, "Emerging anti-cancer antibodies and combination therapies targeting HER3/ERBB3", Human Vaccines and Immunotherapeutics, US, (Mar. 11, 2015), vol. 12, No. 3, doi:10.1080/21645515.2015.1102809, ISSN 2164-5515, pp. 576-592, XP055405052 [I] 1-15 * whole document, especially section "Monoclonal Antibodies Targeting HER3" and Tables 1, 2*.

Shuiliang Wang et al, "Therapeutic targeting of erbB3 with MM-121/SAR256212 enhances antitumor activity of paclitaxel against erbB2-overexpressing breast cancer", Breast Cancer Research, Current Medicine Group Ltd, GB, (Oct. 29, 2013), vol. 15, No. 5, doi:10.1186/BCR3563, ISSN 1465-5411, p. R101, XP021169114 [I] 1-15 * the whole document.

* cited by examiner

[Fig. 1a]

| Antibody | | CDR1 | CDR2 | CDR3 | |
|---|---|---|---|---|---|
| 442P | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DLHMGPE | GPFDY | WGQGTLVTVSS |
| 442S1 | EVQLLESGGGLVQPGGSLRLSCAASGFTFS | DYDMS | WVRQAPGKGLEWVS | DLDSGSIYYADSVQG | RFTISRDNSKNTLYLQMNSLRAEDTAVYYCAK | DLHMGPE | GPFDY | WGQGTLVTVSS |
| 442S4 | EVQLLESGGGLVQPGGSLRLSCAASGFTFS | DYDMS | WVRQAPGKGLEWVS | SYPDSSTDYADSVQG | RFTISRDNSKNTLYLQMNSLRAEDTAVYYCAK | DLHMGPE | GPFDY | WGQGTLVTVSS |
| 442S5 | EVQLLESGGGLVQPGGSLRLSCAASGFTFS | DYDMS | WVRQAPGKGLEWVS | SIEPDFGSSIYYADSVRG | RFTISRDNSKNTLYLQMNSLRAEDTAVYYCAK | DLHMGPE | GPFDY | WGQGTLVTVSS |
| 442S6 | EVQLLESGGGLVQPGGSLRLSCAASGFTFS | DYDMS | WVRQAPGKGLEWVS | SIEPDSGSIYYADSVQG | RFTISRDNSKNTLYLQMNSLRAEDTAVYYCAK | DLHMGPE | GPFDY | WGQGTLVTVSS |
| 442S9 | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DRHMWPE | GPFDY | WGQGTLVTVSS |
| 442S10 | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DRHMWPE | GPFDY | WGQGTLVTVSS |
| 442M3 | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DRHMWPE | GPFDY | WGQGTLVTVSS |
| 442M4 | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DLHMGPE | GPFDY | WGQGTLVTVSS |
| 442M5 | EVQLLESGGGLVQPGGSLRLSCAASGFTFS | DYDMS | WVRQAPGKGLEWVS | DLDSGSIYYADSVQG | RFTISRDNSKNTLYLQMNSLRAEDTAVYYCAK | DLHMGPE | GPFDY | WGQGTLVTVSS |
| 442M6 | EVQLLESGGGLVQPGGSLRLSCAASGFTFS | DYDMS | WVRQAPGKGLEWVS | SIEPDSGSIYYADSVQG | RFTISRDNSKNTLYLQMNSLRAEDTAVYYCAK | DRHMWPE | GPFDY | WGQGTLVTVSS |
| 442M7 | EVQLLESGGGLVQPGGSLRLSCAASGFTFS | DYDMS | WVRQAPGKGLEWVS | STEPDGSTYYADSVQG | RFTISRDNSKNTLYLQMNSLRAEDTAVYYCAK | DLHMGPE | GPFDY | WGQGTLVTVSS |
| 442M8 | EVQLLESGGGLVQPGGSLRLSCAASGFTFS | DYDMS | WVRQAPGKGLEWVS | SYPDSGSIYYADSVQG | RFTISRDNSKNTLYLQMNSLRAEDTAVYYCAK | DLHMGPE | GPFDY | WGQGTLVTVSS |
| 442M10 | EVQLLESGGGLVQPGGSLRLSCAASGFTFS | DYDMS | WVRQAPGKGLEWVS | SYPDSGSTYYADSVQG | RFTISRDNSKNTLYLQMNSLRAEDTAVYYCAK | DLHWPE | GPFDY | WGQGTLVTVSS |
| 442M11 | EVQLLESGGGLVQPGGSLRLSCAASGFTFS | DYDMS | WVRQAPGKGLEWVS | STEPDGSILYADSVQG | RFTISRDNSKNTLYLQMNSLRAEDTAVYYCAK | DLHMGPE | GPFDY | WGQGTLVTVSS |
| 472P | EVQLLESGGGLVQPGGSLRLSCAASGFTFS | DYDMS | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 472S1 | EVQLLESGGGLVQPGGSLRLSCAASGFTFS | WYDMT | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 472S2 | EVQLLESGGGLVQPGGSLRLSCAASGFTFS | WYDLA | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 472S3 | EVQLLESGGGLVQPGGSLRLSCAASGFTFS | MYDMS | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 472S4 | EVQLLESGGGLVQPGGSLRLSCAASGFTFS | WYDIAW | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 472M1 | EVQLLESGGGLVQPGGSLRLSCAASGFTFS | WYDLS | WVRQAPGKGLEWVS | SGISYDGGNITYADSVKG | RFTISRDNSKNTLYLQMNSLRAEDTAVYYCARD | PSWCLQDLCYYADGMD | WGQGTLVTVSS | |
| 451P | EVQLLESGGGLVQPGGSLRLSCAASGFTFS | DYDMS | WVRQAPGKGLEWVS | SAIYYDSGSIYYADSAKG | RFTISRDNSKNTLYLQMNSLRAEDTAVYYCAK | DRLFVSD | STFDY | WGQGTLVTVSS |
| 451M1 | EVQLLESGGGLVQPGGSLRLSCAASGFTFS | DYDMS | WVRQAPGKGLEWVS | SAIYYDSGSIYYADSAKG | RFTISRDNSKNTLYLQMNSLRAEDTAVYYCAK | DRLFMSD | STFDY | WGQGTLVTVSS |
| 451M2 | EVQLLESGGGLVQPGGSLRLSCAASGFTFS | DYDMS | WVRQAPGKGLEWVS | SAIYYDSGSIYYADSAKG | RFTISRDNSKNTLYLQMNSLRAEDTAVYYCAK | DRLFASD | STFDY | WGQGTLVTVSS |
| 451M3 | EVQLLESGGGLVQPGGSLRLSCAASGFTFS | HYDMS | WVRQAPGKGLEWVS | SAIYYDSGSIYYADSAKG | RFTISRDNSKNTLYLQMNSLRAEDTAVYYCAK | DRLFASD | STFDY | WGQGTLVTVSS |
| 451M4 | EVQLLESGGGLVQPGGSLRLSCAASGFTFS | HYDMS | WVRQAPGKGLEWVS | SAIYYDSGSIYYADSAKG | RFTISRDNSKNTLYLQMNSLRAEDTAVYYCAK | DRLFASD | STFDY | WGQGTLVTVSS |
| 451M5 | EVQLLESGGGLVQPGGSLRLSCAASGFTFS | HYDMS | WVRQAPGKGLEWVS | SAIYYDSGSIYYADSAKG | RFTISRDNSKNTLYLQMNSLRAEDTAVYYCAK | DRLFASD | STFDY | WGQGTLVTVSS |
| 451M6 | EVQLLESGGGLVQPGGSLRLSCAASGFTFS | HYDMS | WVRQAPGKGLEWVS | SAIYYDSGSIYYADSAKG | RFTISRDNSKNTLYLQMNSLRAEDTAVYYCAK | DRLFESD | STFDY | WGQGTLVTVSS |
| 451M7 | EVQLLESGGGLVQPGGSLRLSCAASGFTFS | YYDMS | WVRQAPGKGLEWVS | SAIYYDSGSIYYADSAKG | RFTISRDNSKNTLYLQMNSLRAEDTAVYYCAK | DRLFESD | STFDY | WGQGTLVTVSS |

[Fig. 1b]

| Antibody | CDR1 | CDR2 | CDR3 |
|---|---|---|---|
| 442P | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442S1 | QSVLTQPPSASGTPGQRVTISCSGSSSNIGSNSVSWYQQLPGTAPKLLIYSDNHRPSGVPDRFSGSKSGTSASLAISGLRSEDEADYYCQGWDTSLSGHVFGGGTKLTVLG | | |
| 442S2 | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442S4 | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442S5 | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442S6 | QSVLTQPPSASGTPGQRVTISCSGSNSGSWYQQLPGTAPKLLIYADNWRPSGVPDRFSGSKSGTSASLAISGLRSEDEADYYCAAWDSSLSGYVFGGGTKLTVLG | | |
| 442S9 | QSVLTQPPSASGTPGQRVTISCSGSSSNIGSGSWYQQLPGTAPKLLIYADNHRPSGVPDRFSGSKSGTSASLAISGLRSEDEADYYCAAWDSSLSGYVFGGGTKLTVLG | | |
| 442S10 | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442M3 | QSVLTQPPSASGTPGQRVTISCSGSNSGSWYQQLPGTAPKLLIYADNWRPSGVPDRFSGSKSGTSASLAISGLRSEDEADYYCAAWDSSLSGYVFGGGTKLTVLG | | |
| 442M4 | QSVLTQPPSASGTPGQRVTISCSGSSSNIGSNSVSWYQQLPGTAPKLLIYSDNHRPSGVPDRFSGSKSGTSASLAISGLRSEDEADYYCVGWDSSLYGHVFGGGTKLTVLG | | |
| 442M5 | QSVLTQPPSASGTPGQRVTISCSGSSSNIGSNSVSWYQQLPGTAPKLLIYSDNHRPSGVPDRFSGSKSGTSASLAISGLRSEDEADYYCHAWDSSLWGDMFGGGTKLTVLG | | |
| 442M6 | QSVLTQPPSASGTPGQRVTISCSGSSSNIGSNSVSWYQQLPGTAPKLLIYADNWRPSGVPDRFSGSKSGTSASLAISGLRSEDEADYYCAAWDSSLSGYVFGGGTKLTVLG | | |
| 442M7 | QSVLTQPPSASGTPGQRVTISCSGSSSNIGSNSVSWYQQLPGTAPKLLIYSDNHRPSGVPDRFSGSKSGTSASLAISGLRSEDEADYYCAAWDSSLSGYVFGGGTKLTVLG | | |
| 442M8 | QSVLTQPPSASGTPGQRVTISCSGSSSNIGSNSVSWYQQLPGTAPKLLIYSDNHRPSGVPDRFSGSKSGTSASLAISGLRSEDEADYYCHAWDSSLYDVFGGGTKLTVLG | | |
| 442M10 | QSVLTQPPSASGTPGQRVTISCSGSSSNIGSNSVSWYQQLPGTAPKLLIYADNFRPSGVPDRFSGSKSGTSASLAISGLRSEDEADYYCAAWDSSLSGYVFGGGTKLTVLG | | |
| 442M11 | QSVLTQPPSASGTPGQRVTISCSGSSSNIGSNSVSWYQQLPGTAPKLLIYSDNHRPSGVPDRFSGSKSGTSASLAISGLRSEDEADYYCHAWDSSLSGDFFGGGTKLTVLG | | |
| 472P | QSVLTQPPSASGTPGQRVTISCSGSGSSNIGSNSVSWYQQLPGTAPKLLIYADSNRPSGVPDRFSGSKSGTSASLAISGLRSEDEADYYCGSWDYSLSGYVFGGGTKLTVLG | | |
| 472S1 | QSVLTQPPSASGTPGQRVTISCSGSGSSNIGSNSVSWYQQLPGTAPKLLIYADSNRPSGVPDRFSGSKSGTSASLAISGLRSEDEADYYCGSWDYSLSGYVFGGGTKLTVLG | | |
| 472S2 | QSVLTQPPSASGTPGQRVTISCSGSGSSNIGSNSVSWYQQLPGTAPKLLIYADSNRPSGVPDRFSGSKSGTSASLAISGLRSEDEADYYCGSWDYSLSGYVFGGGTKLTVLG | | |
| 472S3 | QSVLTQPPSASGTPGQRVTISCSGSGSSNIGSNSVSWYQQLPGTAPKLLIYADSNRPSGVPDRFSGSKSGTSASLAISGLRSEDEADYYCGSWDYSLSGYVFGGGTKLTVLG | | |
| 472S4 | QSVLTQPPSASGTPGQRVTISCSGSGSSNIGSNSVSWYQQLPGTAPKLLIYADSNRPSGVPDRFSGSKSGTSASLAISGLRSEDEADYYCGSWDYSLSGYVFGGGTKLTVLG | | |
| 472M1 | QSVLTQPPSASGTPGQRVTISCSGSGSSNIGSNSVTMYQQLPGTAPKLLIYADSNRPSGVPDRFSGSKSGTSASLAISGLRSEDEADYYCGSWDYSLSGYVFGGGTKLTVLG | | |
| 451P | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M1 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M2 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M3 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M4 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M5 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M6 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |
| 451M7 | QSVLTQPPSASGTPGQRVTISCSGSSPSNIGNNSVTMYQQLPGTAPKLLIYMDSHRPSGVPDRFSGSKSGTSASLAISGLRSEDEADYYCGSWDASLNGYVFGGGTKLTVLG | | |

[Fig. 2]
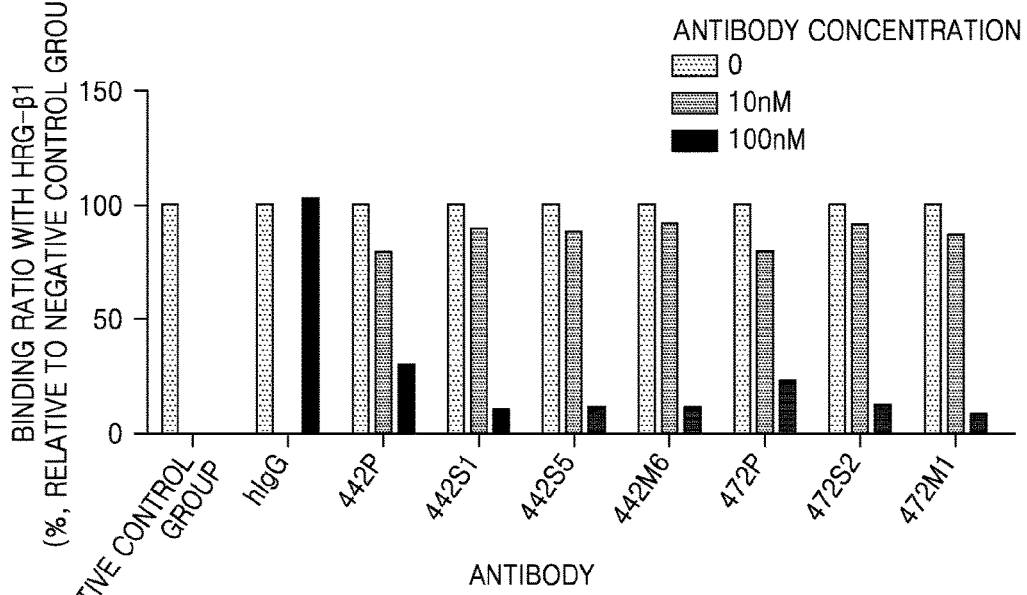
[Fig. 3]
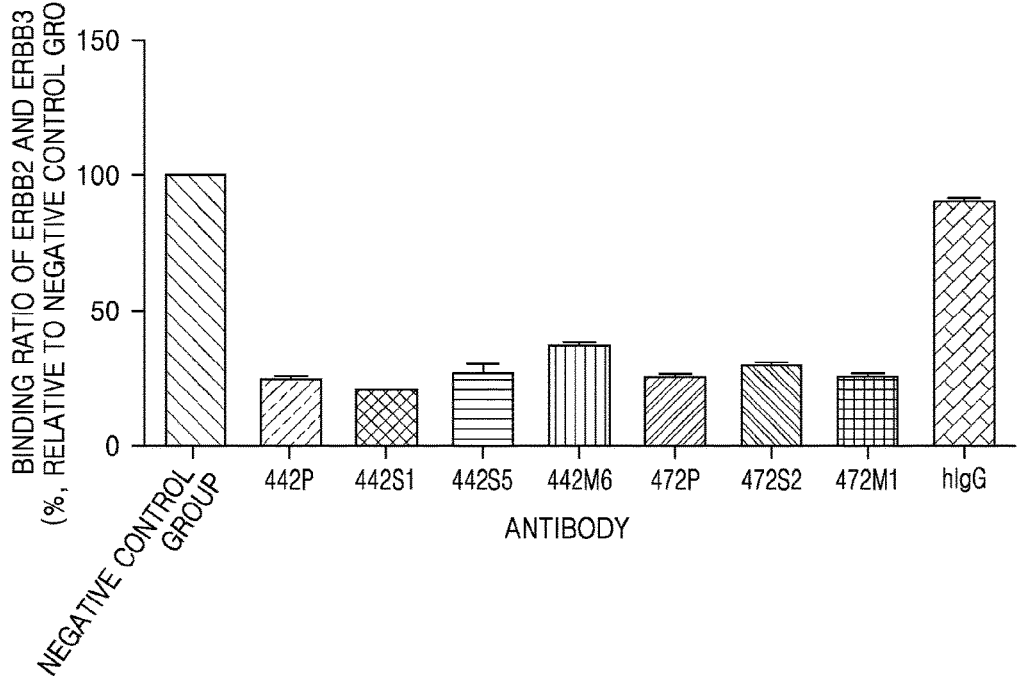

[Fig. 4a]
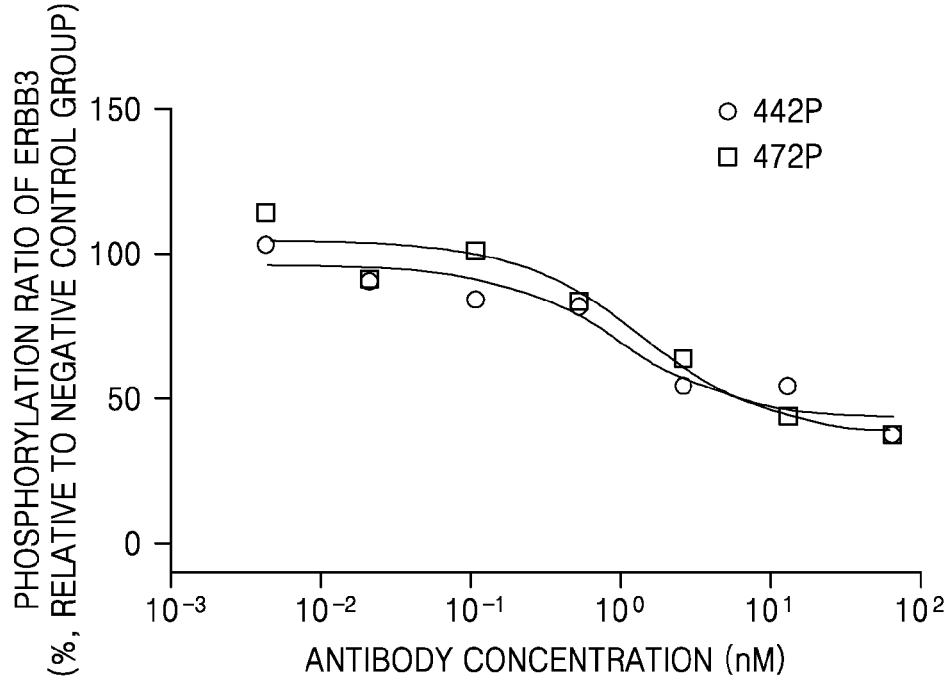
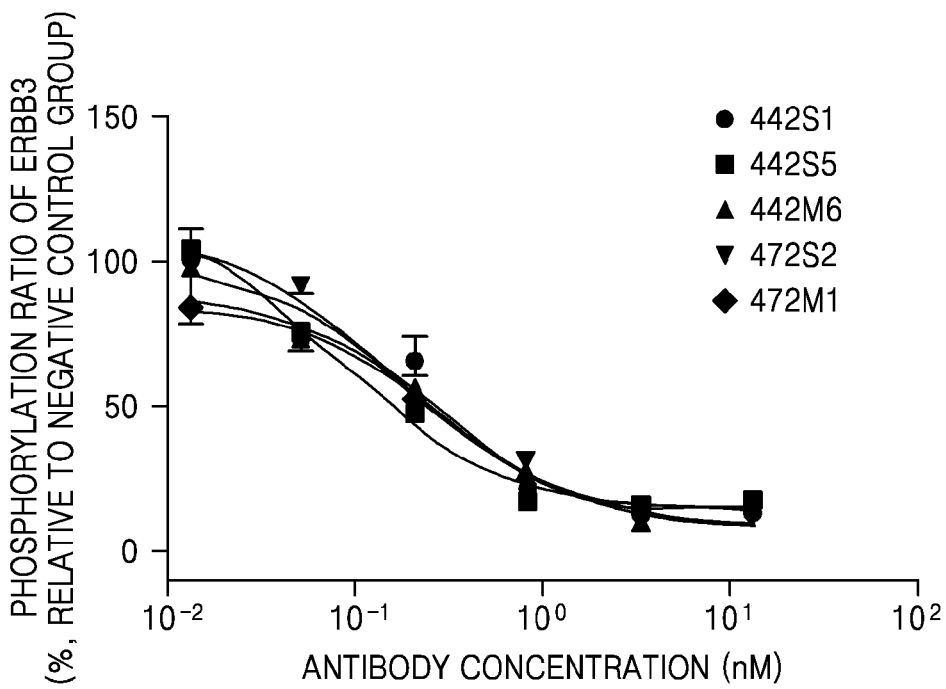

[Fig. 4b]
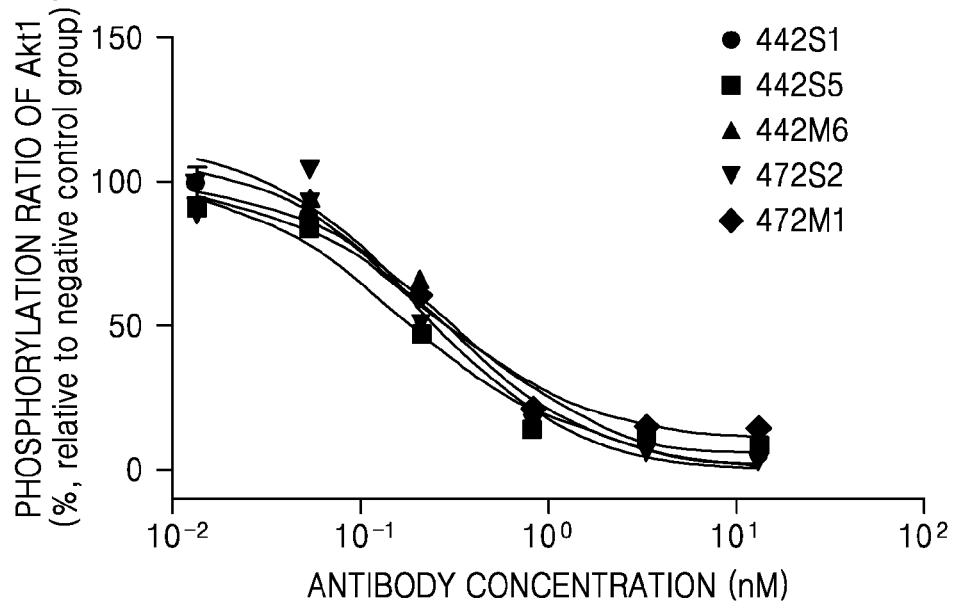
[Fig. 5]
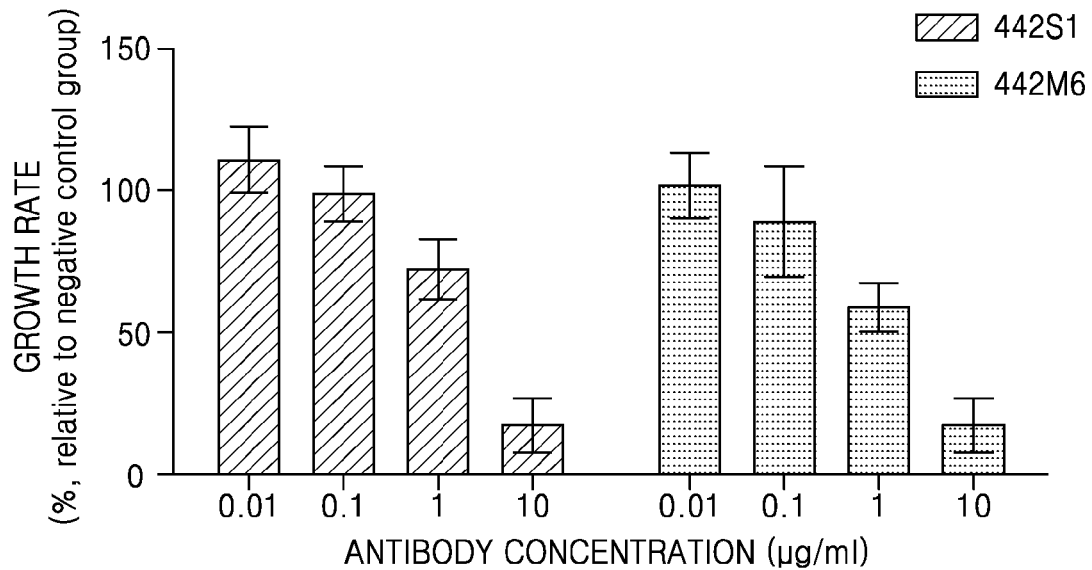

[Fig. 6]
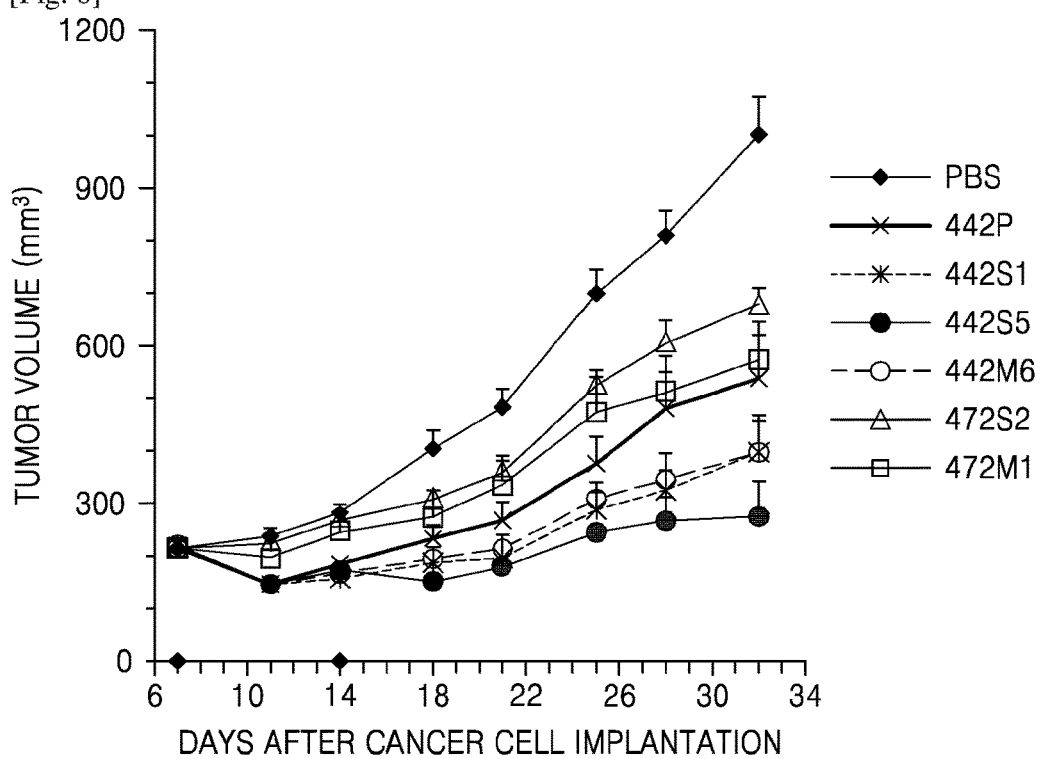
[Fig. 7]
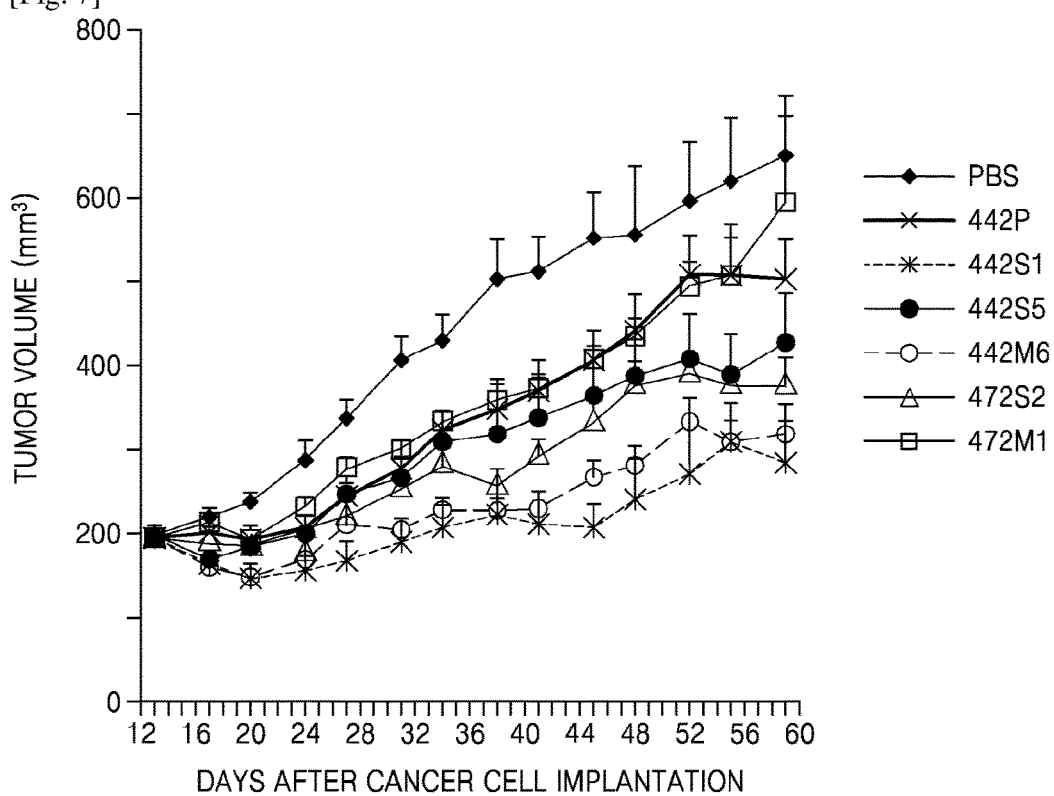

[Fig. 8]
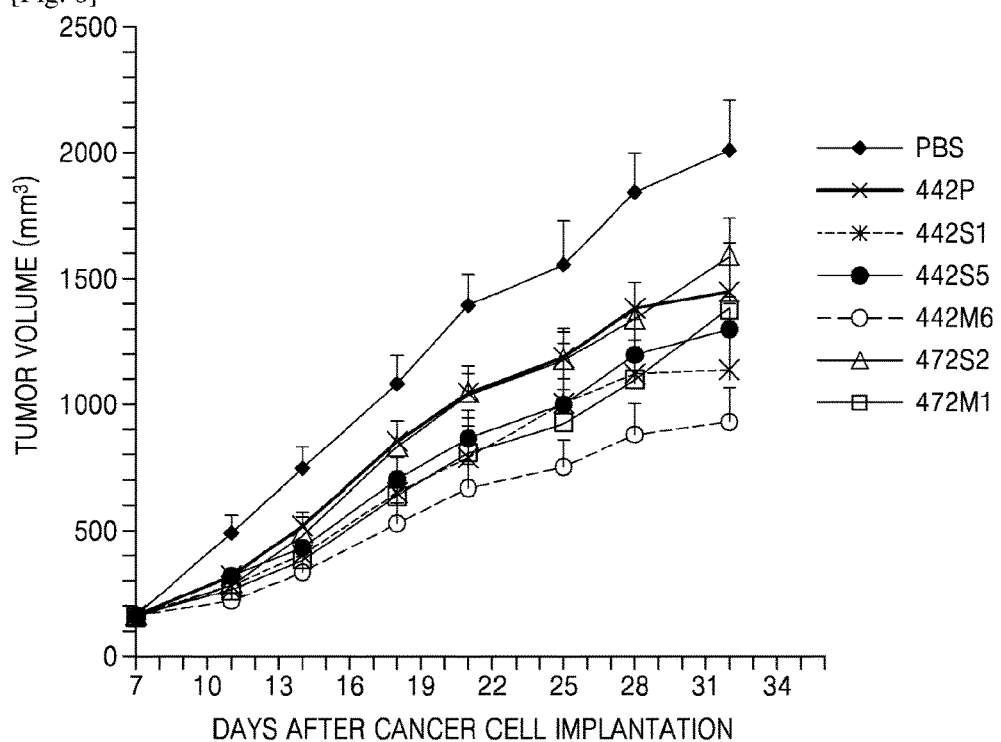
[Fig. 9]
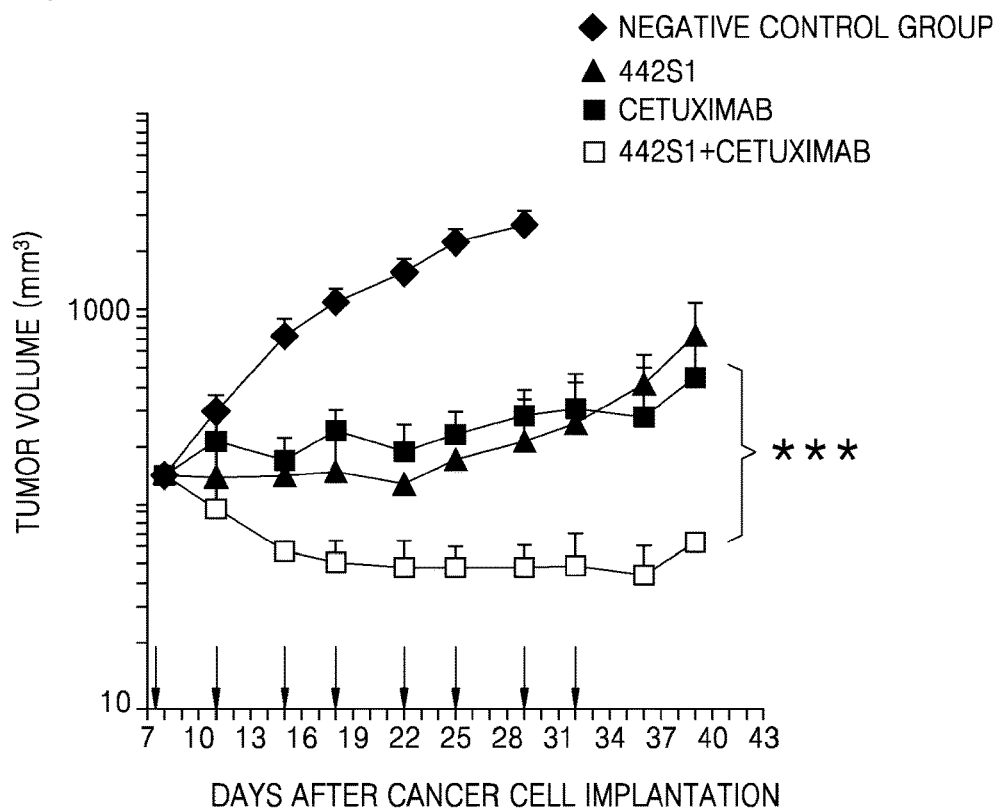

[Fig. 10]
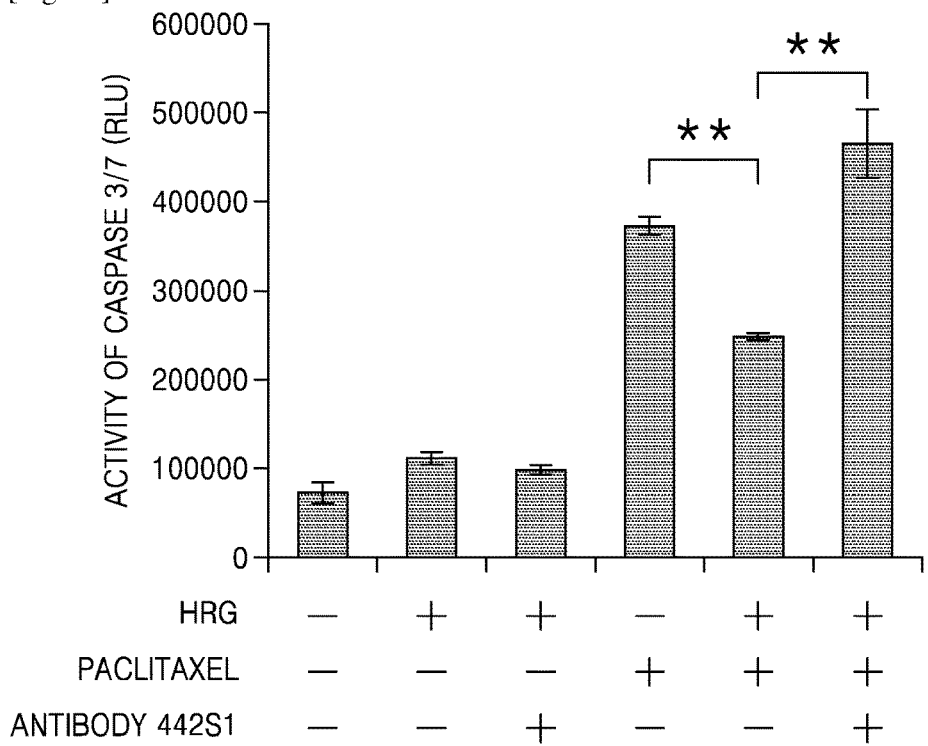
[Fig. 11]
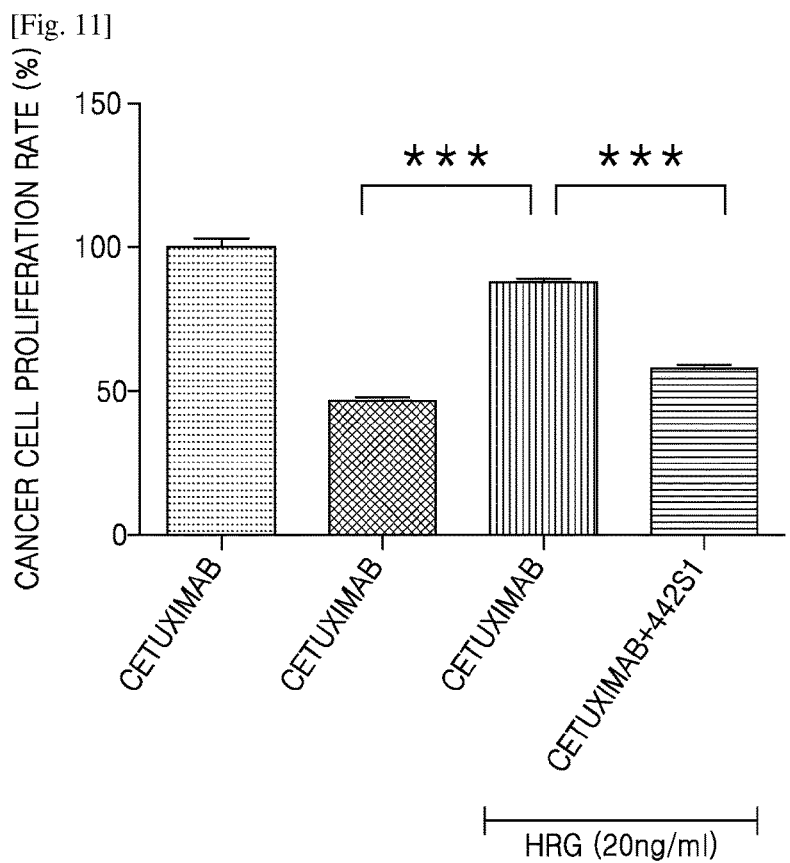

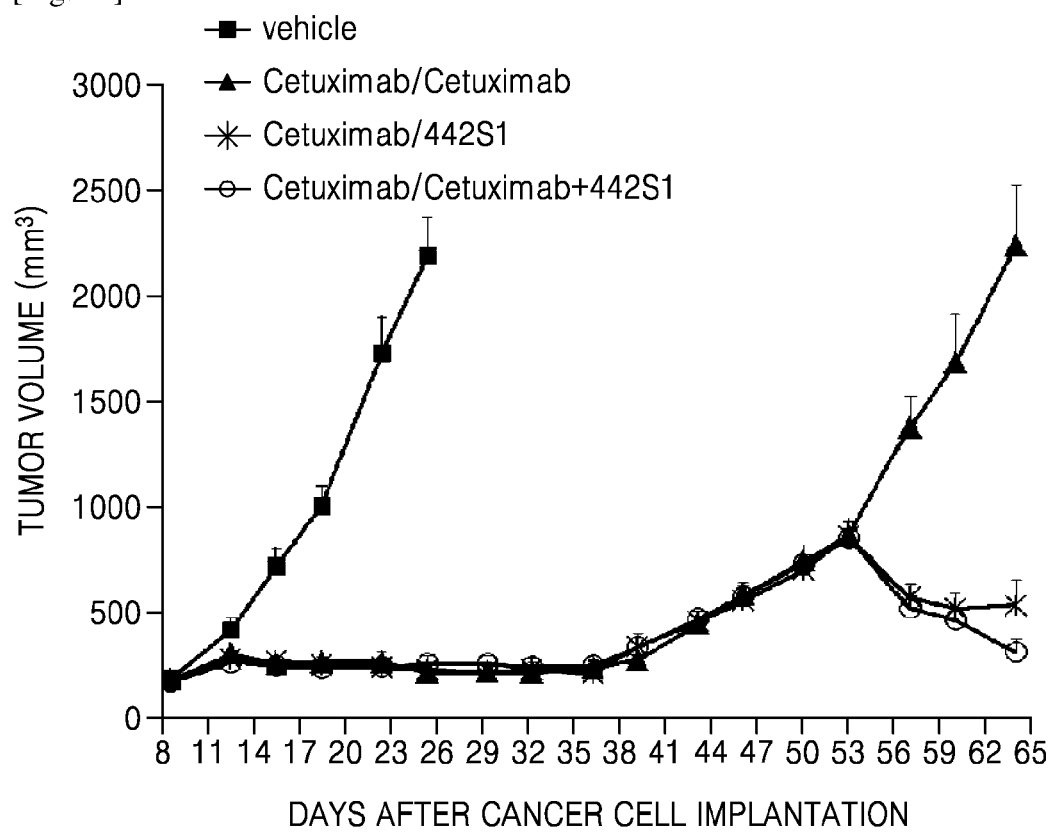
[Fig. 12]

SEQUENCE LISTING

```
<160> NUMBER OF SEQ ID NOS: 103

<210> SEQ ID NO 1
<211> LENGTH: 121
<212> TYPE: PRT
<213> ORGANISM: Artificial Sequence
<220> FEATURE:
<223> OTHER INFORMATION: Heavy chain variable region of antibody 442P

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Tyr Pro Asp Ser Gly Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110
```

```
Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Heavy chain variable region of antibody 442S1

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Thr Ile Asp Leu Asp Ser Gly Ser Ile Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Tyr Trp Gly
            100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Heavy chain variable region of antibody 442S2

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Tyr Pro Asp Ser Gly Ser Thr Asp Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Heavy chain variable region of antibody 442S4
```

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Glu Pro Asp Phe Gly Ser Ser Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110

Gln Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Heavy chain variable region of antibody 442S5

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ile Ile Glu Pro Asp Ser Gly Ser Ile Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110

Gln Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Heavy chain variable region of antibody 442S6

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

```
Ser Ser Ile Tyr Pro Asp Ser Gly Ser Thr Asp Tyr Ala Asp Ser Val
        50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg His Met Trp Pro Glu Gly Pro Phe Asp Tyr Trp Gly
            100                 105                 110

Gln Gly Thr Leu Val Thr Val Ser Ser
            115                 120
```

<210> SEQ ID NO 7
<211> LENGTH: 121
<212> TYPE: PRT
<213> ORGANISM: Artificial Sequence
<220> FEATURE:
<223> OTHER INFORMATION: Heavy chain variable region of antibody 442S9

<400> SEQUENCE: 7

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Asp Met Ser Trp Val Arg Gln Ala Pro Gly Lys Gly Leu Glu Trp Val
            35                  40                  45

Ser Ser Ile Tyr Pro Asp Ser Gly Ser Thr Tyr Tyr Ala Asp Ser Val
        50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg His Met Trp Pro Glu Gly Pro Phe Asp Tyr Trp Gly
            100                 105                 110

Gln Gly Thr Leu Val Thr Val Ser Ser
            115                 120
```

<210> SEQ ID NO 8
<211> LENGTH: 121
<212> TYPE: PRT
<213> ORGANISM: Artificial Sequence
<220> FEATURE:
<223> OTHER INFORMATION: Heavy chain variable region of antibody 442S10

<400> SEQUENCE: 8

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Asp Met Ser Trp Val Arg Gln Ala Pro Gly Lys Gly Leu Glu Trp Val
            35                  40                  45

Ser Ser Ile Tyr Pro Asp Ser Gly Ser Thr Tyr Tyr Ala Asp Ser Val
        50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg His Met Trp Pro Glu Gly Pro Phe Asp Tyr Trp Gly
```

```
                    100                 105                 110

Gln Gly Thr Leu Val Thr Val Ser Ser
            115                 120

<210> SEQ ID NO 9
<211> LENGTH: 121
<212> TYPE: PRT
<213> ORGANISM: Artificial Sequence
<220> FEATURE:
<223> OTHER INFORMATION: Heavy chain variable region of antibody 442M3

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Tyr Pro Asp Ser Gly Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg His Met Trp Pro Glu Gly Pro Phe Asp Tyr Trp Gly
            100                 105                 110

Gln Gly Thr Leu Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: Heavy chain variable region of antibody 442M4

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Thr Ile Asp Leu Asp Ser Gly Ser Ile Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110

Gln Gly Thr Leu Val Thr Val Ser Ser
            115                 120

<210> SEQ ID NO 11
<211> LENGTH: 121
<212> TYPE: PRT
<213> ORGANISM: Artificial Sequence
<220> FEATURE:
```

<223> OTHER INFORMATION: Heavy chain variable region of antibody 442M5

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Thr Ile Asp Leu Asp Ser Gly Ser Ile Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110

Gln Gly Thr Leu Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: Heavy chain variable region of antibody 442M6

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Glu Pro Asp Ser Gly Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg His Met Trp Pro Glu Gly Pro Phe Asp Tyr Trp Gly
            100                 105                 110

Gln Gly Thr Leu Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: Heavy chain variable region of antibody 442M7

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val

```
                35                  40                  45
Ser Thr Ile Glu Pro Asp Ser Gly Ser Thr Tyr Tyr Ala Asp Ser Val
         50                  55                  60

Gln Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu His Met Gly Pro Glu Gly Pro Phe Tyr Trp Gly
                100                 105                 110

Gln Gly Thr Leu Val Thr Val Ser Ser
            115                 120

<210> SEQ ID NO 14
<211> LENGTH: 121
<212> TYPE: PRT
<213> ORGANISM: Artificial Sequence
<220> FEATURE:
<223> OTHER INFORMATION: Heavy chain variable region of antibody 442M8

<400> SEQUENCE: 14

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Asp Met Ser Trp Val Arg Gln Ala Pro Gly Lys Gly Leu Glu Trp Val
             35                  40                  45

Ser Ser Ile Tyr Pro Asp Ser Gly Ser Thr Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu His Met Gly Pro Glu Gly Pro Phe Tyr Trp Gly
                100                 105                 110

Gln Gly Thr Leu Val Thr Val Ser Ser
            115                 120

<210> SEQ ID NO 15
<211> LENGTH: 121
<212> TYPE: PRT
<213> ORGANISM: Artificial Sequence
<220> FEATURE:
<223> OTHER INFORMATION: Heavy chain variable region of antibody 442M10

<400> SEQUENCE: 15

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Asp Met Ser Trp Val Arg Gln Ala Pro Gly Lys Gly Leu Glu Trp Val
             35                  40                  45

Ser Ser Ile Tyr Pro Asp Ser Gly Ser Thr Tyr Ala Asp Ser Val
         50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Asp Leu His Met Trp Pro Glu Gly Pro Phe Asp Tyr Trp Gly
            100                 105                 110

Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Heavy chain variable region of antibody 442M11

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Thr Ile Glu Pro Asp Tyr Gly Ser Thr Leu Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Met Gly Pro Glu Gly Pro Phe Asp Tyr Trp Gly
            100                 105                 110

Gln Gly Thr Leu Val Thr Val Ser Ser
        115                 120

<210> SEQ ID NO 17
<211> LENGTH: 127
<212> TYPE: PRT
<213> ORGANISM: Artificial Sequence
<220> FEATURE:
<223> OTHER INFORMATION: Heavy chain variable region of antibody 472P

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Gly Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Trp Cys Leu Gln Asp Leu Cys Tyr Tyr Ala Asp
            100                 105                 110

Gly Met Asp Val Trp Gly Gln Gly Thr Leu Val Thr Val Ser Ser
            115                 120                 125

<210> SEQ ID NO 18
<211> LENGTH: 127
<212> TYPE: PRT
<213> ORGANISM: Artificial Sequence
```

```
<220> FEATURE:
<223> OTHER INFORMATION: Heavy chain variable region of antibody 472S1

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Met Thr Trp Val Arg Gln Ala Pro Gly Lys Gly Leu Glu Trp Val
        35                  40                  45

Ser Gly Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Trp Cys Leu Gln Asp Leu Cys Tyr Tyr Ala Asp
            100                 105                 110

Gly Met Asp Val Trp Gly Gln Gly Thr Leu Val Thr Val Ser Ser
        115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Heavy chain variable region of antibody 472S2

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Leu Ala Trp Val Arg Gln Ala Pro Gly Lys Gly Leu Glu Trp Val
        35                  40                  45

Ser Gly Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Trp Cys Leu Gln Asp Leu Cys Tyr Tyr Ala Asp
            100                 105                 110

Gly Met Asp Val Trp Gly Gln Gly Thr Leu Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Heavy chain variable region of antibody 472S3

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30
```

```
Asp Met Ser Trp Val Arg Gln Ala Pro Gly Lys Gly Leu Glu Trp Val
            35                  40                  45

Ser Gly Ile Ser Tyr Asp Gly Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Ser Trp Cys Leu Gln Asp Leu Cys Tyr Tyr Ala Asp
               100                 105                 110

Gly Met Asp Val Trp Gly Gln Gly Thr Leu Val Thr Val Ser Ser
               115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Heavy chain variable region of antibody 472S4

<400> SEQUENCE: 21

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                20                  25                  30

Asp Ile Ala Trp Val Arg Gln Ala Pro Gly Lys Gly Leu Glu Trp Val
            35                  40                  45

Ser Gly Ile Ser Tyr Asp Gly Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Ser Trp Cys Leu Gln Asp Leu Cys Tyr Tyr Ala Asp
               100                 105                 110

Gly Met Asp Val Trp Gly Gln Gly Thr Leu Val Thr Val Ser Ser
               115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: Heavy chain variable region of antibody 472M1

<400> SEQUENCE: 22

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                20                  25                  30

Asp Leu Ser Trp Val Arg Gln Ala Pro Gly Lys Gly Leu Glu Trp Val
            35                  40                  45

Ser Gly Ile Ser Tyr Asp Gly Gly Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Asp Pro Ser Trp Cys Leu Gln Asp Leu Cys Tyr Tyr Ala Asp
            100                 105                 110

Gly Met Asp Val Trp Gly Gln Gly Thr Leu Val Thr Val Ser Ser
            115                 120                 125

<210> SEQ ID NO 23
<211> LENGTH: 121
<212> TYPE: PRT
<213> ORGANISM: Artificial Sequence
<220> FEATURE:
<223> OTHER INFORMATION: Heavy chain variable region of antibody 451P

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Ala Ile Tyr Tyr Asp Ser Gly Ser Ile Tyr Tyr Ala Asp Ser Ala
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Arg Leu Phe Val Ser Asp Ser Thr Phe Asp Tyr Trp Gly
            100                 105                 110

Gln Gly Thr Leu Val Thr Val Ser Ser
            115                 120

<210> SEQ ID NO 24
<211> LENGTH: 121
<212> TYPE: PRT
<213> ORGANISM: Artificial Sequence
<220> FEATURE:
<223> OTHER INFORMATION: Heavy chain variable region of antibody 451M1

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Ala Ile Tyr Tyr Asp Ser Gly Ser Ile Tyr Tyr Ala Asp Ser Ala
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Arg Leu Phe Met Ser Asp Ser Thr Phe Asp Tyr Trp Gly
            100                 105                 110

Gln Gly Thr Leu Val Thr Val Ser Ser
            115                 120

<210> SEQ ID NO 25
<211> LENGTH: 121
<212> TYPE: PRT

```
<213> ORGANISM: Artificial Sequence
<220> FEATURE:
<223> OTHER INFORMATION: Heavy chain variable region of antibody 451M2

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Phe Ala Ser Asp Ser Thr Phe Asp Tyr Trp Gly
            100                 105                 110

Gln Gly Thr Leu Val Thr Val Ser Ser
        115                 120

<210> SEQ ID NO 26
<211> LENGTH: 121
<212> TYPE: PRT
<213> ORGANISM: Artificial Sequence
<220> FEATURE:
<223> OTHER INFORMATION: Heavy chain variable region of antibody 451M3

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asp Met Ser Trp Val Arg Gln Ala Pro Gly Lys Gly Leu Glu Trp Val
        35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Phe Ala Ser Asp Ser Thr Phe Asp Tyr Trp Gly
            100                 105                 110

Gln Gly Thr Leu Val Thr Val Ser Ser
        115                 120

<210> SEQ ID NO 27
<211> LENGTH: 121
<212> TYPE: PRT
<213> ORGANISM: Artificial Sequence
<220> FEATURE:
<223> OTHER INFORMATION: Heavy chain variable region of antibody 451M4

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30
```

Asp Met Ser Trp Val Arg Gln Ala Pro Gly Lys Gly Leu Glu Trp Val
            35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Phe Ala Ser Asp Ser Thr Phe Asp Tyr Trp Gly
            100                 105                 110

Gln Gly Thr Leu Val Thr Val Ser Ser
            115                 120

<210> SEQ ID NO 28
<211> LENGTH: 121
<212> TYPE: PRT
<213> ORGANISM: Artificial Sequence
<220> FEATURE:
<223> OTHER INFORMATION: Heavy chain variable region of antibody 451M5

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Phe Glu Ser Asp Ser Thr Phe Asp Tyr Trp Gly
            100                 105                 110

Gln Gly Thr Leu Val Thr Val Ser Ser
            115                 120

<210> SEQ ID NO 29
<211> LENGTH: 121
<212> TYPE: PRT
<213> ORGANISM: Artificial Sequence
<220> FEATURE:
<223> OTHER INFORMATION: Heavy chain variable region of antibody 451M6

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asp Met Ser Trp Val Arg Gln Ala Pro Gly Lys Gly Leu Glu Trp Val
            35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95

Ala Lys Asp Arg Leu Phe Glu Ser Asp Ser Thr Phe Asp Tyr Trp Gly
            100                 105                 110

Gln Gly Thr Leu Val Thr Val Ser Ser
        115                 120

<210> SEQ ID NO 30
<211> LENGTH: 121
<212> TYPE: PRT
<213> ORGANISM: Artificial Sequence
<220> FEATURE:
<223> OTHER INFORMATION: Heavy chain variable region of antibody 451M7

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ser Trp Val Arg Gln Ala Pro Gly Lys Gly Leu Glu Trp Val
        35                  40                  45

Ser Ala Ile Tyr Tyr Asp Ser Gly Ser Ile Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Phe Glu Ser Asp Ser Thr Phe Asp Tyr Trp Gly
            100                 105                 110

Gln Gly Thr Leu Val Thr Val Ser Ser
        115                 120

<210> SEQ ID NO 31
<211> LENGTH: 111
<212> TYPE: PRT
<213> ORGANISM: Artificial Sequence
<220> FEATURE:
<223> OTHER INFORMATION: Light chain variable region of antibody 442P

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 32
<211> LENGTH: 111
<212> TYPE: PRT
<213> ORGANISM: Artificial Sequence
<220> FEATURE:
```

<223> OTHER INFORMATION: Light chain variable region of antibody 442S1

<400> SEQUENCE: 32

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Ser Val Ser Trp Tyr Gln Gln Leu Pro Gly Thr Ala Pro Lys Leu Leu
        35                  40                  45
Ile Tyr Ser Asp Asn His Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gln Gly Trp Asp Thr Ser Leu
                85                  90                  95
Ser Gly His Val Phe Gly Gly Gly Thr Lys Leu Thr Val Leu Gly
            100                 105                 110
```

<210> SEQ ID NO 33
<211> LENGTH: 111
<212> TYPE: PRT
<213> ORGANISM: Artificial Sequence
<220> FEATURE:
<223> OTHER INFORMATION: Light chain variable region of antibody 442S2

<400> SEQUENCE: 33

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Ser Val Ser Trp Tyr Gln Gln Leu Pro Gly Thr Ala Pro Lys Leu Leu
        35                  40                  45
Ile Tyr Ser Asp Asn His Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Ser Ser Leu
                85                  90                  95
Ser Gly Tyr Val Phe Gly Gly Gly Thr Lys Leu Thr Val Leu Gly
            100                 105                 110
```

<210> SEQ ID NO 34
<211> LENGTH: 111
<212> TYPE: PRT
<213> ORGANISM: Artificial Sequence
<220> FEATURE:
<223> OTHER INFORMATION: Light chain variable region of antibody 442S4

<400> SEQUENCE: 34

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Ser Val Ser Trp Tyr Gln Gln Leu Pro Gly Thr Ala Pro Lys Leu Leu
        35                  40                  45
Ile Tyr Ser Asp Asn His Arg Pro Ser Gly Val Pro Asp Arg Phe Ser
    50                  55                  60
Gly Ser Lys Ser Gly Thr Ser Ala Ser Leu Ala Ile Ser Gly Leu Arg
```

```
                 65                  70                  75                  80
Ser Glu Asp Glu Ala Asp Tyr Tyr Cys Ala Ala Trp Asp Ser Ser Leu
                     85                  90                  95

Ser Gly Tyr Val Phe Gly Gly Gly Thr Lys Leu Thr Val Leu Gly
                100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Light chain variable region of antibody 442S5

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ser Val Ser Trp Tyr Gln Gln Leu Pro Gly Thr Ala Pro Lys Leu Leu
            35                  40                  45

Ile Tyr Ser Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                    85                  90                  95

Ser Gly Tyr Val Phe Gly Gly Gly Thr Lys Leu Thr Val Leu Gly
                100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Light chain variable region of antibody 442S6

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ser Gly Ser Trp Tyr Gln Gln Leu Pro Gly Thr Ala Pro Lys Leu Leu
            35                  40                  45

Ile Tyr Ala Asp Asn Trp Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                    85                  90                  95

Ser Gly Tyr Val Phe Gly Gly Gly Thr Lys Leu Thr Val Leu Gly
                100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Light chain variable region of antibody 442S9

<400> SEQUENCE: 37
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ser Gly Ser Trp Tyr Gln Gln Leu Pro Gly Thr Ala Pro Lys Leu Leu
            35                  40                  45

Ile Tyr Ala Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110
```

<210> SEQ ID NO 38
<211> LENGTH: 111
<212> TYPE: PRT
<213> ORGANISM: Artificial Sequence
<220> FEATURE:
<223> OTHER INFORMATION: Light chain variable region of antibody 442S10

<400> SEQUENCE: 38

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ser Val Ser Trp Tyr Gln Gln Leu Pro Gly Thr Ala Pro Lys Leu Leu
            35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110
```

<210> SEQ ID NO 39
<211> LENGTH: 111
<212> TYPE: PRT
<213> ORGANISM: Artificial Sequence
<220> FEATURE:
<223> OTHER INFORMATION: Light chain variable region of antibody 442M3

<400> SEQUENCE: 39

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ser Gly Ser Trp Tyr Gln Gln Leu Pro Gly Thr Ala Pro Lys Leu Leu
            35                  40                  45

Ile Tyr Ala Asp Asn Trp Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
```

```
                85                  90                  95

Ser Gly Tyr Val Phe Gly Gly Gly Thr Lys Leu Thr Val Leu Gly
            100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Light chain variable region of antibody 442M4

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Val Gly Trp Asp Ser Ser Leu
                85                  90                  95

Tyr Gly His Val Phe Gly Gly Gly Thr Lys Leu Thr Val Leu Gly
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Light chain variable region of antibody 442M5

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys His Ala Trp Asp Ser Ser Leu
                85                  90                  95

Trp Gly Asp Val Phe Gly Gly Gly Thr Lys Leu Thr Val Leu Gly
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Light chain variable region of antibody 442M6

<400> SEQUENCE: 42

Gln Ser Val Leu Thr Gln Pro Pro Ser Ala Ser Gly Thr Pro Gly Gln
1               5                   10                  15
```

-continued

Arg Val Thr Ile Ser Cys Ser Gly Ser Ser Ser Asn Ile Gly Ser Asn
            20                  25                  30

Ser Gly Ser Trp Tyr Gln Gln Leu Pro Gly Thr Ala Pro Lys Leu Leu
        35                  40                  45

Ile Tyr Ala Asp Asn Trp Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Light chain variable region of antibody 442M7

<400> SEQUENCE: 43

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Light chain variable region of antibody 442M8

<400> SEQUENCE: 44

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys His Ala Trp Asp Ser Ser Leu
                85                  90                  95

Tyr Val Asp Val Phe Gly Gly Gly Thr Lys Leu Thr Val Leu Gly

<210> SEQ ID NO 45
<211> LENGTH: 111
<212> TYPE: PRT
<213> ORGANISM: Artificial Sequence
<220> FEATURE:
<223> OTHER INFORMATION: Light chain variable region of antibody 442M10

<400> SEQUENCE: 45

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Asn Phe Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Ser Leu
                85                  90                  95

Ser Gly Tyr Val Phe Gly Gly Gly Thr Lys Leu Thr Val Leu Gly
            100                 105                 110
```

<210> SEQ ID NO 46
<211> LENGTH: 111
<212> TYPE: PRT
<213> ORGANISM: Artificial Sequence
<220> FEATURE:
<223> OTHER INFORMATION: Light chain variable region of antibody 442M11

<400> SEQUENCE: 46

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ser Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys His Ala Trp Asp Ser Ser Leu
                85                  90                  95

Ser Gly Asp Phe Phe Gly Gly Gly Thr Lys Leu Thr Val Leu Gly
            100                 105                 110
```

<210> SEQ ID NO 47
<211> LENGTH: 111
<212> TYPE: PRT
<213> ORGANISM: Artificial Sequence
<220> FEATURE:
<223> OTHER INFORMATION: Light chain variable region of antibody 472P

<400> SEQUENCE: 47

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Ser Val Ser Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Light chain variable region of antibody 472S1

<400> SEQUENCE: 48

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
            100                 105                 110

<210> SEQ ID NO 49
<211> LENGTH: 111
<212> TYPE: PRT
<213> ORGANISM: Artificial Sequence
<220> FEATURE:
<223> OTHER INFORMATION: Light chain variable region of antibody 472S2

<400> SEQUENCE: 49

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
            100                 105                 110
```

```
<210> SEQ ID NO 50
<211> LENGTH: 111
<212> TYPE: PRT
<213> ORGANISM: Artificial Sequence
<220> FEATURE:
<223> OTHER INFORMATION: Light chain variable region of antibody 472S3

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Light chain variable region of antibody 472S4

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Light chain variable region of antibody 472M1

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45
```

```
Ile Tyr Ala Asp Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
            100                 105                 110

<210> SEQ ID NO 53
<211> LENGTH: 111
<212> TYPE: PRT
<213> ORGANISM: Artificial Sequence
<220> FEATURE:
<223> OTHER INFORMATION: Light chain variable region of antibody 451P

<400> SEQUENCE: 53

Gln Ser Val Leu Thr Gln Pro Pro Ser Ala Ser Gly Thr Pro Gly Gln
 1               5                  10                  15

Arg Val Thr Ile Ser Cys Ser Gly Ser Pro Ser Asn Ile Gly Asn Asn
                20                  25                  30

Ser Val Thr Trp Tyr Gln Gln Leu Pro Gly Thr Ala Pro Lys Leu Leu
            35                  40                  45

Ile Tyr Tyr Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Asn Gly Tyr Val Phe Gly Gly Gly Thr Lys Leu Thr Val Leu Gly
            100                 105                 110

<210> SEQ ID NO 54
<211> LENGTH: 111
<212> TYPE: PRT
<213> ORGANISM: Artificial Sequence
<220> FEATURE:
<223> OTHER INFORMATION: Light chain variable region of antibody 451M1

<400> SEQUENCE: 54

Gln Ser Val Leu Thr Gln Pro Pro Ser Ala Ser Gly Thr Pro Gly Gln
 1               5                  10                  15

Arg Val Thr Ile Ser Cys Ser Gly Ser Pro Ser Asn Ile Gly Asn Asn
                20                  25                  30

Ser Val Thr Trp Tyr Gln Gln Leu Pro Gly Thr Ala Pro Lys Leu Leu
            35                  40                  45

Ile Tyr Tyr Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Asn Gly Tyr Val Phe Gly Gly Gly Thr Lys Leu Thr Val Leu Gly
            100                 105                 110

<210> SEQ ID NO 55
<211> LENGTH: 111
<212> TYPE: PRT
```

<213> ORGANISM: Artificial Sequence
<220> FEATURE:
<223> OTHER INFORMATION: Light chain variable region of antibody 451M2

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Light chain variable region of antibody 451M3

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Light chain variable region of antibody 451M4

<400> SEQUENCE: 57

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Light chain variable region of antibody 451M5

<400> SEQUENCE: 58

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Light chain variable region of antibody 451M6

<400> SEQUENCE: 59

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Light chain variable region of antibody 451M7

```
<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Pro Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Gly Tyr Val Phe Gly Gly Gly Thr Lys Leu Thr Val Leu Gly
                100                 105                 110

<210> SEQ ID NO 61
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 61

Asp Tyr Asp Met Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 62

Trp Tyr Asp Met Thr
1               5

<210> SEQ ID NO 63
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 63

Trp Tyr Asp Leu Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 64

Trp Tyr Asp Met Ser
1               5

<210> SEQ ID NO 65
<211> LENGTH: 5
```

```
<212> TYPE: PRT
<213> ORGANISM: Artificial Sequence
<220> FEATURE:
<223> OTHER INFORMATION: Heavy chain CDR1

<400> SEQUENCE: 65

Trp Tyr Asp Ile Ala
1               5

<210> SEQ ID NO 66
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 66

Trp Tyr Asp Leu Ser
1               5

<210> SEQ ID NO 67
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 67

His Tyr Asp Met Ser
1               5

<210> SEQ ID NO 68
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 68

Tyr Tyr Asp Met Ser
1               5

<210> SEQ ID NO 69
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 69

Ser Ile Tyr Pro Asp Ser Gly Ser Thr Tyr Tyr Ala Asp Ser Val Gln
1               5                   10                  15

Gly

<210> SEQ ID NO 70
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 70

Thr Ile Asp Leu Asp Ser Gly Ser Ile Tyr Tyr Ala Asp Ser Val Gln
1               5                   10                  15

Gly
```

```
<210> SEQ ID NO 71
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 71

Ser Ile Tyr Pro Asp Ser Gly Ser Thr Asp Tyr Ala Asp Ser Val Gln
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 72

Ser Ile Glu Pro Asp Phe Gly Ser Ser Tyr Tyr Ala Asp Ser Val Arg
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 73

Ile Ile Glu Pro Asp Ser Gly Ser Ile Tyr Tyr Ala Asp Ser Val Gln
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 74

Ser Ile Glu Pro Asp Ser Gly Ser Thr Asp Tyr Ala Asp Ser Val Gln
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 75

Thr Ile Glu Pro Asp Ser Gly Ser Thr Tyr Tyr Ala Asp Ser Val Gln
1               5                   10                  15

Ser

<210> SEQ ID NO 76
<211> LENGTH: 17
<212> TYPE: PRT
```

<213> ORGANISM: Artificial Sequence
<220> FEATURE:
<223> OTHER INFORMATION: Heavy chain CDR2

<400> SEQUENCE: 76

Gly Ile Ser Tyr Asp Gly Gly Asn Thr Tyr Tyr Ala Asp Ser Val Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 77

Ala Ile Tyr Tyr Asp Ser Gly Ser Ile Tyr Tyr Ala Asp Ser Ala Lys
1               5                   10                  15
Gly

<210> SEQ ID NO 78
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 78

Asp Leu His Met Gly Pro Glu Gly Pro Phe Asp Tyr
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 79

Asp Arg His Met Trp Pro Glu Gly Pro Phe Asp Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 80

Asp Leu His Met Trp Pro Glu Gly Pro Phe Asp Tyr
1               5                   10

<210> SEQ ID NO 81
<211> LENGTH: 18
<212> TYPE: PRT
<213> ORGANISM: Artificial Sequence
<220> FEATURE:
<223> OTHER INFORMATION: Heavy chain CDR3

<400> SEQUENCE: 81

Asp Pro Ser Trp Cys Leu Gln Asp Leu Cys Tyr Tyr Ala Asp Gly Met
1               5                   10                  15
Asp Val

```
<210> SEQ ID NO 82
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 82

Asp Arg Leu Phe Val Ser Asp Ser Thr Phe Asp Tyr
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 83

Asp Arg Leu Phe Met Ser Asp Ser Thr Phe Asp Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 84

Asp Arg Leu Phe Ala Ser Asp Ser Thr Phe Asp Tyr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 85

Asp Arg Leu Phe Glu Ser Asp Ser Thr Phe Asp Tyr
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Light chain CDR1

<400> SEQUENCE: 86

Ser Gly Ser Ser Ser Asn Ile Gly Ser Asn Ser Val Ser
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Light chain CDR1

<400> SEQUENCE: 87

Ser Gly Ser Ser Ser Asn Ile Gly Ser Asn Ser Gly Ser
1               5                   10
```

<210> SEQ ID NO 88
<211> LENGTH: 7
<212> TYPE: PRT
<213> ORGANISM: Artificial Sequence
<220> FEATURE:
<223> OTHER INFORMATION: Light chain CDR2

<400> SEQUENCE: 88

Ser Asp Asn His Arg Pro Ser
1               5

<210> SEQ ID NO 89
<211> LENGTH: 7
<212> TYPE: PRT
<213> ORGANISM: Artificial Sequence
<220> FEATURE:
<223> OTHER INFORMATION: Light chain CDR2

<400> SEQUENCE: 89

Ala Asp Asn Trp Arg Pro Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Light chain CDR2

<400> SEQUENCE: 90

Ala Asp Asn His Arg Pro Ser
1               5

<210> SEQ ID NO 91
<211> LENGTH: 7
<212> TYPE: PRT
<213> ORGANISM: Artificial Sequence
<220> FEATURE:
<223> OTHER INFORMATION: Light chain CDR2

<400> SEQUENCE: 91

Ala Asp Asn Phe Arg Pro Ser
1               5

<210> SEQ ID NO 92
<211> LENGTH: 7
<212> TYPE: PRT
<213> ORGANISM: Artificial Sequence
<220> FEATURE:
<223> OTHER INFORMATION: Light chain CDR2

<400> SEQUENCE: 92

Ala Asp Ser Asn Arg Pro Ser
1               5

<210> SEQ ID NO 93
<211> LENGTH: 7
<212> TYPE: PRT
<213> ORGANISM: Artificial Sequence
<220> FEATURE:
<223> OTHER INFORMATION: Light chain CDR2

<400> SEQUENCE: 93

Tyr Asp Ser His Arg Pro Ser
1               5

<210> SEQ ID NO 94
<211> LENGTH: 11
<212> TYPE: PRT
<213> ORGANISM: Artificial Sequence
<220> FEATURE:
<223> OTHER INFORMATION: Light chain CDR3

<400> SEQUENCE: 94

Ala Ala Trp Asp Ser Ser Leu Ser Gly Tyr Val
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Light chain CDR3

<400> SEQUENCE: 95

Gln Gly Trp Asp Thr Ser Leu Ser Gly His Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Light chain CDR3

<400> SEQUENCE: 96

Val Gly Trp Asp Ser Ser Leu Tyr Gly His Val
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Light chain CDR3

<400> SEQUENCE: 97

His Ala Trp Asp Ser Ser Leu Trp Gly Asp Val
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Light chain CDR3

<400> SEQUENCE: 98

His Ala Trp Asp Ser Ser Leu Tyr Val Asp Val
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Light chain CDR3

<400> SEQUENCE: 99

His Ala Trp Asp Ser Ser Leu Ser Gly Asp Phe
1               5                   10

<210> SEQ ID NO 100

```
<211> LENGTH: 11
<212> TYPE: PRT
<213> ORGANISM: Artificial Sequence
<220> FEATURE:
<223> OTHER INFORMATION: Light chain CDR3

<400> SEQUENCE: 100

Gly Ser Trp Asp Tyr Ser Leu Ser Gly Tyr Val
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Light chain CDR3

<400> SEQUENCE: 101

Gly Ser Trp Asp Ala Ser Leu Asn Gly Tyr Val
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 102

Thr Ile Glu Pro Asp Tyr Gly Ser Thr Leu Tyr Ala Asp Ser Val Gln
1               5                   10                  15
Gly

<210> SEQ ID NO 103
<211> LENGTH: 13
<212> TYPE: PRT
<213> ORGANISM: Artificial Sequence
<220> FEATURE:
<223> OTHER INFORMATION: Light chain CDR1

<400> SEQUENCE: 103

Ser Gly Ser Pro Ser Asn Ile Gly Asn Asn Ser Val Thr
1               5                   10
```

ANTIBODY SPECIFICALLY BINDING TO ERBB3 AND USE THEREOF

REFERENCE TO A SEQUENCE LISTING

The Sequence Listing written in file "GN-53072-US_Revised Sequence Listing(Clean).txt", 74,005 bytes, machine format IBM-PC, MS-Windows operating system, is hereby incorporated by reference in its entirety for all purposes.

TECHNICAL FIELD

One or more example embodiments relate to an antibody specifically binding to a receptor tyrosine kinase ErbB3 protein or an antigen-binding fragment of the antibody, a method of preparing the same, and use thereof.

BACKGROUND ART

The epidermal growth factor receptor (EGFR or ErbB) family of receptor tyrosine kinases includes ErbB1 (known also as epidermal growth factor receptor (EGFR)), ErbB2 (known also as human epidermal growth factor receptor 2 (HER2)), ErbB3 (known also as HER3), and ErbB4 (known also as HER4). The receptor tyrosine kinases of the ErbB family may form a homodimer or heterodimer by combination with a ligand and may activate the signal transduction pathway of mitogen-activated protein kinase kinase (MAP2K, MEK, or MAPKK)/mitogen-activated protein kinase (MAPK), or the signal transduction pathway of phosphoinositide 3-kinase (PI3K)/protein kinase B (PKB or Akt). The ErbB family of proteins is reported to be related to the occurrence, progress, or prognosis of cancer.

Erbitux® (Cetuximab) or Tarceva® (Erlotinib) as ErbB1 inhibitors and Herceptin® (Trastuzumab) or Tyverb® (Lapatinib) as ErbB2 inhibitors, are commercially available anti-cancer drugs. However, a large number of patients are unresponsive to these anti-cancer drugs, and these anti-cancer drugs are accompanied with development of resistance. A specific inhibitor antibody to ErbB3 or ErbB4 has not yet been made commercially available.

Therefore, there is a need for the development of new anti-cancer drugs that may cope with the genetic diversity of cancer and overcome resistance to anti-cancer drugs.

DETAILED DESCRIPTION OF THE INVENTION

Technical Problem

One or more example embodiments include an antibody specifically binding to ErbB3, or an antigen-binding fragment thereof.

One or more example embodiments include a pharmaceutical composition for prevention or treatment of a disease related to the activation or overexpression of ErbB3 protein.

One or more example embodiments include a method of prevention or treatment of a disease related to the activation or overexpression of ErbB3 protein in an individual.

Technical Solution

This application claims the benefit of Korean Patent Application No. 10-2015-0173281, filed on Dec. 7, 2015, in the Korean Intellectual Property Office, the disclosure of which is incorporated herein in its entirety by reference.

Reference will now be made in detail to example embodiments, which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, an antibody specifically binding to ErbB3 or an antigen-binding fragment of the antibody includes:

a heavy chain variable region including at least one amino acid sequence selected from the group consisting of SEQ ID NOs: 61 to 85, and 102;

a light chain variable region including at least one amino acid sequence selected from the group consisting of SEQ ID NOs: 86 to 101, and 103; or the heavy chain variable region and the light chain variable region.

There are five types of heavy chains denoted by γ, δ, α, μ, and ε. The type of heavy chain defines the class of antibody. The heavy chain types α and γ each chain consists of approximately 450 amino acids, whereas μ and ε each chain consists of approximately 550 amino acids. Each heavy chain has two regions, i.e., the variable region and the constant region.

There are two types of light chains denoted by λ and κ. Each light chain consists of approximately 211 to 217 amino acids. Each human antibody contains only one type of light chain. Each light chain contains two successive domains including one constant region and one variable region.

The variable region refers to a region of the antibody which binds to an antigen.

The heavy chain variable region may include: a complementarity-determining region-H1 (CDR-H1) including an amino acid sequence selected from the group consisting of SEQ ID. NOs: 61 to 68; a CDR-H2 including an amino acid sequence selected from SEQ ID NOs: 69 to 77, and 102; and a CDR-H3 including an amino acid sequence selected from SEQ ID NOs: 78 to 85. For example, the heavy chain variable region may include an amino acid sequence selected from the group consisting of SEQ ID NOs: 1 to 30. The term "complementarity-determining region (CDR)" refers to a site of the variable region of an antibody that imparts binding specificity of the antibody or antigen-binding fragment thereof to an antigen.

The light chain variable region may include: a CDR-L1 including an amino acid sequence selected from the group consisting of SEQ ID NOs: 86, 87, and 103; a CDR-L2 including an amino acid sequence selected from the group consisting of SEQ ID NOs: 88 to 93; and a CDR-L3 including an amino acid sequence selected from the group consisting of SEQ ID NOs: 94 to 101. For example, the light chain variable region may include an amino acid sequence selected from the group consisting of SEQ ID NOs: 31 to 60.

The antibody or the antigen-binding fragment thereof may include a heavy chain variable region selected from the group consisting of heavy chain variable regions CDR-H1, CDR-H2, and CDR-H3, which represent amino acid sequences listed in Table 5.

TABLE 5

| No. | CDR-H1 | CDR-H2 | CDR-H3 |
|---|---|---|---|
| 1 | DYDMS (SEQ ID NO: 61) | SIYPDSGSTYYADSVQG (SEQ ID NO: 69) | DLHMGPEGPFDY (SEQ ID NO: 78) |
| 2 | DYDMS (SEQ ID NO: 61) | TIDLDSGSIYYADSVQG (SEQ ID NO: 70) | DLHMGPEGPFDY (SEQ ID NO: 78) |
| 3 | DYDMS (SEQ ID NO: 61) | SIYPDSGSTDYADSVQG (SEQ ID NO: 71) | DLHMGPEGPFDY (SEQ ID NO: 78) |
| 4 | DYDMS (SEQ ID NO: 61) | SIEPDFGSSYYADSVRG (SEQ ID NO: 72) | DLHMGPEGPFDY (SEQ ID NO: 78) |
| 5 | DYDMS (SEQ ID NO: 61) | IIEPDSGSIYYADSVQG (SEQ ID NO: 73) | DLHMGPEGPFDY (SEQ ID NO: 78) |
| 6 | DYDMS (SEQ ID NO: 61) | SIYPDSGSTDYADSVQG (SEQ ID NO: 71) | DRHMWPEGPFDY (SEQ ID NO: 79) |
| 7 | DYDMS (SEQ ID NO: 61) | SIYPDSGSTYYADSVQG (SEQ ID NO: 69) | DRHMWPEGPFDY (SEQ ID NO: 79) |
| 8 | DYDMS (SEQ ID NO: 61) | SIYPDSGSTYYADSVQG (SEQ ID NO: 69) | DRHMWPEGPFDY (SEQ ID NO: 79) |
| 9 | DYDMS (SEQ ID NO: 61) | SIYPDSGSTYYADSVQG (SEQ ID NO: 69) | DRHMWPEGPFDY (SEQ ID NO: 79) |
| 10 | DYDMS (SEQ ID NO: 61) | TIDLDSGSIYYADSVQG (SEQ ID NO: 70) | DLHMGPEGPFDY (SEQ ID NO: 78) |
| 11 | DYDMS (SEQ ID NO: 61) | TIDLDSGSIYYADSVQG (SEQ ID NO: 70) | DLHMGPEGPFDY (SEQ ID NO: 78) |
| 12 | DYDMS (SEQ ID NO: 61) | SIEPDSGSTDYADSVQG (SEQ ID NO: 74) | DRHMWPEGPFDY (SEQ ID NO: 79) |
| 13 | DYDMS (SEQ ID NO: 61) | TIEPDSGSTYYADSVQS (SEQ ID NO: 75) | DLHMGPEGPFDY (SEQ ID NO: 78) |
| 14 | DYDMS (SEQ ID NO: 61) | SIYPDSGSTYYADSVQG (SEQ ID NO: 69) | DLHMGPEGPFDY (SEQ ID NO: 78) |
| 15 | DYDMS (SEQ ID NO: 61) | SIYPDSGSTDYADSVQG (SEQ ID NO: 70) | DLHMWPEGPFDY (SEQ ID NO: 80) |
| 16 | DYDMS (SEQ ID NO: 61) | TIEPDYGSTLYADSVQG (SEQ ID NO: 75) | DLHMGPEGPFDY (SEQ ID NO: 78) |
| 17 | DYDMS (SEQ ID NO: 61) | GISYDGGNTYYADSVKG (SEQ ID NO: 76) | DPSWCLQDLCYYADGMDV (SEQ ID NO: 81) |
| 18 | WYDMT (SEQ ID NO: 62) | GISYDGGNTYYADSVKG (SEQ ID NO: 76) | DPSWCLQDLCYYADGMDV (SEQ ID NO: 81) |
| 19 | WYDLA (SEQ ID NO: 63) | GISYDGGNTYYADSVKG (SEQ ID NO: 76) | DPSWCLQDLCYYADGMDV (SEQ ID NO: 81) |
| 20 | WYDMS (SEQ ID NO: 64) | GISYDGGNTYYADSVKG (SEQ ID NO: 76) | DPSWCLQDLCYYADGMDV (SEQ ID NO: 81) |
| 21 | WYDIA (SEQ ID NO: 65) | GISYDGGNTYYADSVKG (SEQ ID NO: 76) | DPSWCLQDLCYYADGMDV (SEQ ID NO: 81) |
| 22 | WYDLS (SEQ ID NO: 66) | GISYDGGNTYYADSVKG (SEQ ID NO: 76) | DPSWCLQDLCYYADGMDV (SEQ ID NO: 81) |
| 23 | DYDMS (SEQ ID NO: 61) | AIYYDSGSIYYADSAKG (SEQ ID NO: 77) | DRLFVSDSTFDY (SEQ ID NO: 82) |
| 24 | DYDMS (SEQ ID NO: 61) | AIYYDSGSWYADSAKG (SEQ ID NO: 77) | DRLFMSDSTFDY (SEQ ID NO: 83) |
| 25 | DYDMS (SEQ ID NO: 61) | AIYYDSGSIYYADSAKG (SEQ ID NO: 77) | DRLFASDSTFDY (SEQ ID NO: 84) |
| 26 | HYDMS (SEQ ID NO: 67) | AIYYDSGSIYYADSAKG (SEQ ID NO: 77) | DRLFASDSTFDY (SEQ ID NO: 84) |
| 27 | YYDMS (SEQ ID NO: 68) | AIYYDSGSIYYADSAKG (SEQ ID NO: 77) | DRLFASDSTFDY (SEQ ID NO: 84) |
| 28 | DYDMS (SEQ ID NO: 61) | AIYYDSGSIYYADSAKG (SEQ ID NO: 77) | DRLFESDSTFDY (SEQ ID NO: 85) |
| 29 | HYDMS (SEQ ID NO: 67) | AIYYDSGSIYYADSAKG (SEQ ID NO: 77) | DRLFESDSTFDY (SEQ ID NO: 85) |
| 30 | YYDMS (SEQ ID NO: 68) | AIYYDSGSIYYADSAKG (SEQ ID NO: 77) | DRLFESDSTFDY (SEQ ID NO: 85) |

For example, the antibody or the antigen-binding fragment thereof may include a heavy chain variable region that includes a CDR-H1 including an amino acid sequence of SEQ ID NO: 61, a CDR-H2 including an amino acid sequence of SEQ ID NO: 69, and a CDR-H3 including an amino acid sequence of SEQ ID NO: 78.

The antibody or the antigen-binding fragment thereof may include a light chain variable region selected from the group consisting of light chain variable regions CDR-L1, CDR-L2, and CDR-L3, which include amino acid sequences listed in Table 6.

TABLE 6

| No. | CDR-L1 | CDR-L2 | CDR-L3 |
|---|---|---|---|
| 31 | SGSSSNIGSNSVS (SEQ ID NO: 86) | SDNHRPS (SEQ ID NO: 88) | AAWDSSLSGYV (SEQ ID NO: 94) |
| 32 | SGSSSNIGSNSVS (SEQ ID NO: 86) | SDNHRPS (SEQ ID NO: 88) | QGWDTSLSGHV (SEQ ID NO: 95) |

TABLE 6-continued

| No. | CDR-L1 | CDR-L2 | CDR-L3 |
|---|---|---|---|
| 33 | SGSSSNIGSNSVS (SEQ ID NO: 86) | SDNHRPS (SEQ ID NO: 88) | AAWDSSLSGYV (SEQ ID NO: 94) |
| 34 | SGSSSNIGSNSVS (SEQ ID NO: 86) | SDNHRPS (SEQ ID NO: 88) | AAWDSSLSGYV (SEQ ID NO: 94) |
| 35 | SGSSSNIGSNSVS (SEQ ID NO: 86) | SDNHRPS (SEQ ID NO: 88) | AAWDSSLSGYV (SEQ ID NO: 94) |
| 36 | SGSSSNIGSNSGS (SEQ ID NO: 87) | ADNWRPS (SEQ ID NO: 89) | AAWDSSLSGYV (SEQ ID NO: 94) |
| 37 | SGSSSNIGSNSGS (SEQ ID NO: 87) | ADNHRPS (SEQ ID NO: 90) | AAWDSSLSGYV (SEQ ID NO: 94) |
| 38 | SGSSSNIGSNSVS (SEQ ID NO: 86) | SDNHRPS (SEQ ID NO: 88) | AAWDSSLSGYV (SEQ ID NO: 94) |
| 39 | SGSSSNIGSNSGS (SEQ ID NO: 87) | ADNWRPS (SEQ ID NO: 89) | AAWDSSLSGYV (SEQ ID NO: 94) |
| 40 | SGSSSNIGSNSVS (SEQ ID NO: 86) | SDNHRPS (SEQ ID NO: 88) | VGWDSSLYGHV (SEQ ID NO: 96) |
| 41 | SGSSSNIGSNSVS (SEQ ID NO: 86) | SDNHRPS (SEQ ID NO: 88) | HAWDSSLWGDV (SEQ ID NO: 97) |
| 42 | SGSSSNIGSNSGS (SEQ ID NO: 87) | ADNWRPS (SEQ ID NO: 89) | AAWDSSLSGYV (SEQ ID NO: 94) |
| 43 | SGSSSNIGSNSVS (SEQ ID NO: 86) | SDNHRPS (SEQ ID NO: 88) | AAWDSSLSGYV (SEQ ID NO: 94) |
| 44 | SGSSSNIGSNSVS (SEQ ID NO: 86) | SDNHRPS (SEQ ID NO: 88) | HAWDSSLYVDV (SEQ ID NO: 98) |
| 45 | SGSSSNIGSNSVS (SEQ ID NO: 86) | ADNFRPS (SEQ ID NO: 91) | AAWDSSLSGYV (SEQ ID NO: 94) |
| 46 | SGSSSNIGSNSVS (SEQ ID NO: 86) | SDNHRPS (SEQ ID NO; 88) | HAWDSSLSGDF (SEQ ID NO: 99) |
| 47 | SGSSSNIGSNSVS (SEQ ID NO: 86) | ADSNRPS (SEQ ID NO: 92) | GSWDYSLSGYV (SEQ ID NO: 100) |
| 48 | SGSSSNIGSNSVS (SEQ ID NO: 86) | ADSNRPS (SEQ ID NO: 92) | GSWDYSLSGYV (SEQ ID NO: 100) |
| 49 | SGSSSNIGSNSVS (SEQ ID NO: 86) | ADSNRPS (SEQ ID NO: 92) | GSWDYSLSGYV (SEQ ID NO: 100) |
| 50 | SGSSSNIGSNSVS (SEQ ID NO: 86) | ADSNRPS (SEQ ID NO: 92) | GSWDYSLSGYV (SEQ ID NO: 100) |
| 51 | SGSSSNIGSNSVS (SEQ ID NO: 86) | ADSNRPS (SEQ ID NO: 92) | GSWDYSLSGYV (SEQ ID NO: 100) |
| 52 | SGSSSNIGSNSVS (SEQ ID NO: 86) | ADSNRPS (SEQ ID NO: 92) | GSWDYSLSGYV (SEQ ID NO: 100) |
| 53 | SGSPSNIGNNSVT (SEQ ID NO: 87) | YDSHRPS (SEQ ID NO: 93) | GSWDASLNGYV (SEQ ID NO: 101) |
| 54 | SGSPSNIGNNSVT (SEQ ID NO: 87) | YDSHRPS (SEQ ID NO: 93) | GSWDASLNGYV (SEQ ID NO: 101) |
| 55 | SGSPSNIGNNSVT (SEQ ID NO: 87) | YDSHRPS (SEQ ID NO: 93) | GSWDASLNGYV (SEQ ID NO: 101) |
| 56 | SGSPSNIGNNSVT (SEQ ID NO: 87) | YDSHRPS (SEQ ID NO: 93) | GSWDASLNGYV (SEQ ID NO: 101) |
| 57 | SGSPSNIGNNSVT (SEQ ID NO: 87) | YDSHRPS (SEQ ID NO: 93) | GSWDASLNGYV (SEQ ID NO: 101) |
| 58 | SGSPSNIGNNSVT (SEQ ID NO: 87) | YDSHRPS (SEQ ID NO: 93) | GSWDASLNGYV (SEQ ID NO: 101) |
| 59 | SGSPSN1GNNSVT (SEQ ID NO: 87) | YDSHRPS (SEQ ID NO: 93) | GSWDASLNGYV (SEQ ID NO: 101) |
| 60 | SGSPSNIGNNSVT (SEQ ID NO: 87) | YDSHRPS (SEQ ID NO: 93) | GSWDASLNGYV (SEQ ID NO: 101) |

For example, the antibody or the antigen-binding fragment thereof may include a light chain variable region that includes a CDR-L1 including an amino acid sequence of SEQ ID NO: 86, a CDR-L2 including an amino acid sequence of SEQ ID NO: 88, and a CDR-L3 including an amino acid sequence of SEQ ID NO: 94.

The ErbB3 may be an ErbB3 polypeptide or a fragment thereof. The ErbB3 polypeptide may be a human amino acid sequence with GenBank Accession No. NP_001005915, or a mouse amino acid sequence with GenBank Accession No. NP_034283. The fragment of the ErbB3 polypeptide may be a polypeptide including a partial amino acid sequence of the ErbB3 polypeptide. The ErbB3 is a receptor tyrosine kinase of the epidermal growth factor receptor (EGFR or ErbB) family, and is known also as HER3.

The antibody or the antigen-binding fragment thereof that specifically binds to ErbB3 may have affinity to an ErbB3 polypeptide or a fragment thereof.

The antibody or the antigen-binding fragment thereof may inhibit binding of ErbB3 protein with a material that specifically binds to ErbB3 protein, dimerization of ErbB1 protein and ErbB3 protein, dimerization of ErbB2 protein and ErbB3 protein, phosphorylation of ErbB3 or Akt, or a combination thereof. The material specifically binding to ErbB3 protein may be heregulin (HRG).

The term "antibody" is interchangeably used with "immunoglobulin (Ig)." The whole antibody has a structure including two full-length light chains and two full-length heavy chains, which are connected by disulfide (SS) bonds. The antibody may be, for example, IgA, IgD, IgE, IgG, or IgM. The antibody may be a monoclonal antibody or a polyclonal antibody. The antibody may be an animal-derived antibody, a mouse-human chimeric antibody, a humanized antibody, or a human antibody.

The term "antigen-binding fragment" refers to a fragment of the whole immunoglobulin structure, which may be a part of a polypeptide including an antigen-binding site. For example, the antigen-binding fragment may be scFv, (scFv)$_2$, Fv, Fab, Fab', Fv F(ab')2, or a combination thereof.

The antibody or the antigen-binding fragment thereof may be modified. For example, the antibody or the antigen-binding fragment thereof may be modified by conjugation or binding, glycosylation, tag attachment, or a combination thereof. The antibody may be conjugated with other drugs such as anti-cancer drug. For example, the antibody or the antigen-binding fragment thereof may be conjugated with horseradish peroxidase (HRP), alkaline phosphatase, hapten, biotin, streptavidin, a fluorescent material, a radioactive material, quantum dots, polyethylene glycol (PEG), a histidine tag, or a combination thereof. The fluorescent material may be Alexa Fluor®532, Alexa Fluor®546, Alexa Fluor®568, Alexa Fluor®680, Alexa Fluor®750, Alexa Fluor®790, or Alexa Fluor™350.

According to another aspect of the present disclosure, a pharmaceutical composition for prevention or treatment of a disease related to activation or overexpression of ErbB3 protein includes the antibody or the antigen-binding fragment thereof according to any of the above-described example embodiments.

The antibody, antigen-binding fragment, and ErbB3 protein are the same as described above.

The disease related to the activation or overexpression of ErbB3 protein may be cancer. The cancer may be a solid cancer or a non-solid cancer. Solid cancers refer to the incidence of cancerous tumors in solid organs such as the liver, lung, breast, or skin, whereas non-solid cancers refer to cancers affecting the blood, and so are called blood cancer. For example, the cancer may be selected from the group consisting of breast cancer, skin cancer, head and neck cancer, pancreatic cancer, lung cancer, colon cancer, colorectal cancer, gastric cancer, ovarian cancer, prostate cancer, bladder cancer, uterine cancer, liver cancer, kidney cancer, clear cell sarcoma, melanoma, cerebrospinal tumors, brain cancer, thymoma, mesothelioma, esophageal cancer, biliary tract cancer, testicular cancer, germinal cancer, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, endocrine cancer, and sarcoma.

The term "prevention" refers to any act that suppresses or delays the onset of a disease related to the activation or overexpression of ErbB3 protein by administration of the pharmaceutical composition. The term "treatment" refers to any act that alleviates symptoms of a disease related to the activation or overexpression of ErbB3 protein by administration of the pharmaceutical composition.

The pharmaceutical composition may include a pharmaceutically acceptable carrier. The carrier may be construed as meaning an excipient, a diluent, or an adjuvant. For example, the carrier may be selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, physiological saline, a buffer such as phosphate-buffered saline (PBS), methyl hydroxybenzoate, propyl hydroxybenzoate, talc, magnesium stearate, glycine, histidine, serine, polysorbate, and mineral oil. The pharmaceutical composition may include a filler, an anti-coagulant, a lubricant, a wetting agent, a flavoring agent, an emulsifier, a presentative, or a combination thereof.

The pharmaceutical composition may be formulated in any form using any common method in the art. For example, the pharmaceutical composition may be formulated in oral dosage form (for example, powders, tablets, capsules, syrups, pills, or granules), or parenteral dosage form (for example, injection). The pharmaceutical composition may be prepared in formulation for systemic delivery, or in a formulation for local delivery.

The pharmaceutical composition may further include an anti-cancer drug. The anti-cancer drug may be Cetuximab, Panitumumab, Erlotinib, Gefitinib, Trastuzumab, T-DM1, Pertuzumab, Lapatinib, Paclitaxel, Tamoxifen, Cisplatin, anti-CTLA-4 antibody, anti-PD-1 antibody, anti-PD-L1 antibody, 5-fluorouracil (5FU), Gemcitabine, or a combination thereof. The pharmaceutical composition may include a single composition or separate compositions. For example, the antibody or the antigen-binding fragment thereof of the pharmaceutical composition may be a composition in parenteral dosage form, and the anti-cancer drug may be a composition in oral dosage form.

The pharmaceutical composition may include an effective amount of the antibody or the antigen-binding fragment thereof, an anti-cancer drug, or a combination thereof. The term "effective amount" used herein refers to an amount sufficient to prevent or treat a disease related to activation or overexpression of ErbB3 protein when administered to an individual who needs such prevention or treatment. The effective amount may be appropriately selected depending on a selected cell or individual by one of ordinary skill in the art. For example, the effective amount may be determined depending on disease severity, a patient's age, body weight, health conditions, gender, a patient's drug sensitivity, administration duration, administration route, excretion rate, treatment duration, and other factors, including use of a drug in combination with or at the same time as the pharmaceutical composition, and other factors known in the medical field. The effective amount may be about 0.5 µg to about 2 g, about 1 µg to about 1 g, about 10 µg to about 500 mg, about 100 µg to about 100 mg, or about 1 mg to about 50 mg of the pharmaceutical composition.

A dose of the pharmaceutical composition may be, for example, about 0.001 mg/kg to about 100 mg/kg, about 0.01 mg/kg to about 10 mg/kg, or about 0.1 mg/kg to about 1 mg/kg when administered to an adult. The number of administrations may be, for example, once or multiple times a day, once a week, once in two weeks, once in three weeks, once in four weeks, or once a year.

According to another aspect of the present disclosure, a method of prevention or treatment of a disease related to activation or overexpression of ErbB3 protein in an individual includes administering the antibody or an antigen-binding fragment thereof according to any of the above-described example embodiments to the individual.

The antibody, antigen-binding fragment, ErbB3 protein, disease related to the activation or overexpression of ErbB3 protein, prevention, or treatment may be the same as described above.

The individual may be a mammal, for example, a human, cow, horse, pig, dog, sheep, goat, or cat. The individual may be an individual who suffers from a disease related to the activation or overexpression of ErbB3 protein or who is susceptible to the disease, which may be cancer.

The method may further include administering an anti-cancer drug to the individual. The anti-cancer drug may be administered at the same time with, separately from, or sequentially with the antibody or an antigen-binding fragment thereof according to any of the above-described example embodiments.

For example, the antibody or the antigen-binding fragment thereof, an anti-cancer drug, or a combination thereof may be directly administered to the individual by any method, for example, by oral, intravenous, intramuscular, transdermal, mucosal, intranasal, intratracheal, or subcutaneous administration. The antibody or the antigen-binding fragment thereof, an anti-cancer drug, or a combination thereof may be administered systemically or locally. The antibody or the antigen-binding fragment thereof, an anti-cancer drug, or a combination thereof may be administered alone or together with a pharmaceutically active compound.

A dose of the antibody or the antigen-binding fragment thereof, an anti-cancer drug, or a combination thereof may vary depending on a patient's condition, body weight, disease severity, drug formulation, administration route, and administration duration, and may be appropriately selected by one of ordinary skill in the art. For example, a dose of the antibody or the antigen-binding fragment thereof, an anti-cancer drug, or a combination thereof may be about 0.001 mg/kg to about 100 mg/kg, about 0.01 mg/kg to about 10 mg/kg, or about 0.1 mg/kg to about 1 mg/kg when administered to an adult. The number of administrations may be, for example, once or multiple times a day, once a week, once in two weeks, once in three weeks, once in four weeks, or once a year.

According to another aspect of the present disclosure, a method of prevention or treatment of cancer drug resistance in an individual includes administering the antibody or the antigen-binding fragment of any one of claims 1 to 10 to the individual.

Advantageous Effects of the Invention

As described above, according to the one or more example embodiments, an antibody that specifically binds to ErbB3 or an antigen-binding fragment thereof, and use thereof, are provided. The antibody that specifically binds to ErbB3 or an antigen-binding fragment thereof may be effectively used to prevent or treat a disease related to activation or overexpression of ErbB3 protein.

DESCRIPTION OF THE DRAWINGS

FIGS. 1A and 1B illustrate amino acid sequences and complementarity-determining regions (CDRs) in variable regions of heavy chains (FIG. 1A) and light chains (FIG. 1B) of lead antibodies and modified antibodies thereof;

FIG. 2 is a graph showing the binding affinity (%) of ErbB3 protein and HRG in the presence of anti-ErbB3 antibodies;

FIG. 3 is a graph showing the binding affinity (%) of ErbB2 protein and ErbB3 protein in the presence of anti-ErbB3 antibodies;

FIGS. 4A and 4B are graphs showing phosphorylation ratios (%) of ErbB3 and Akt, respectively, in the presence of anti-ErbB3 antibodies;

FIG. 5 is a graph of relative proliferation (%) of BxPC3 pancreatic cancer cells in the presence of anti-ErbB3 antibodies;

FIG. 6 is a graph of tumor volume ($mm^3$) in a BT474 breast cancer xenograft model after administration of anti-ErbB3 antibodies;

FIG. 7 is a graph of tumor volume ($mm^3$) in a MDA-MB-468 breast cancer xenograft model after administration of anti-ErbB3 antibodies;

FIG. 8 is a graph of tumor volume ($mm^3$) in an A431 skin cancer xenograft model after administration of anti-ErbB3 antibodies;

FIG. 9 is a graph of tumor volume ($mm^3$) in a FaDu head and neck cancer xenograft model after administration of anti-ErbB3 antibodies or combined administration of anti-ErbB3 antibodies and Cetuximab;

FIG. 10 is a graph of the activity of caspase 3/7 (in relative luminance units (RLU)) in breast cancer cells after combined administration of paclitaxel, HRG, and anti-ErbB3 antibody;

FIG. 11 is a graph of cancer cell proliferation rate (%) in colorectal cancer cells after combined administration of Cetuximab, HRG, and anti-ErbB3 antibody; and FIG. 12 is a graph of tumor volume in an Cetuximab-resistant xenograft model after combined administration of Cetuximab and anti-ErbB3 antibody.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Example 1. Preparation of Anti-ErbB3 Antibody

1. Screening of Lead Antibody

To obtain human anti-ErbB3 antibodies, the human synthetic scFv-phage display library (provided by H.B. SHIM of Ewha Womans University, Korea) was screened against ErbB3 protein (R&D systems) to obtain phage displaying scFv fragments that bind to ErbB3.

Nucleic acid sequences encoding the scFV fragments of the obtained phage were analyzed, and amino acid sequences of the VH and VL domains of the scFv fragments that bind to ErbB3 were identified by amino acid sequence analysis. After the sequences of the scFv fragments that bind to ErbB3 were obtained, the VH and VL domains were reconstructed using a Selexis 085 vector (Selexis) encoding IgG1, to thereby assemble the whole antibody gene. The reconstructed expression vectors encoding IgG1 were transformed and expressed at a small scale in Chinese hamster ovary (CHO) cell lines. The expressed anti-ErbB3 antibodies were subjected to measurement of binding affinity to ErbB3 and cellular-based analysis, to thereby screen anti-ErbB3 lead antibodies 442P, 472P, and 451P that inhibit heregulin (HRG)-dependent ErbB3 signal transduction.

2. Screening of Modified Antibodies from Lead Antibodies

Fab-phage display libraries were constructed by introducing mutations into six CDR sites of the screened anti-ErbB3 lead antibodies 442P, 472P, and 451P of Example 1.1 by random mutagenesis. The Fab-phage display libraries were amplified by polymerase chain reaction (PCR) with primers (by Integrated DNA Technologies, Inc.), which were made to order, and Phusion polymerase (New England Biolabs).

The constructed Fab-phage display libraries were screened against the recombinant human ErbB3 protein (R&D systems) to screen for antibodies with improved binding affinity to the recombinant human ErbB3, as compared with the lead antibodies. The screened antibodies were reconstructed to IgG as described in Example 1.1 and transformed and expressed at a small scale in CHO cell lines.

The binding affinity of the anti-ErbB3 antibodies was measured using an Octet® QK384 system (Pall Life Sciences). The antibodies with improved binding affinity compared to the lead antibodies were screened based on the results and subjected to cellular-based analysis to verify efficacy. Amino acid sequences of the variable regions of the anti-ErbB3 lead antibodies and the modified antibodies were analyzed, and complementarity-determining regions (CDRs) were determined according to the Kabat definition. The amino acid sequences (SEQ ID NOs: 1 to 60) in the various regions of heavy chains and light chains of the screened antibodies are presented in FIGS. 1A and 1B, and the amino acid sequences in the CDRs of the heavy chains and light chains are shown in Table 1 and 2, respectively.

TABLE 1

| Antibody | CDR-H1 | CDR-H2 | CDR-H3 |
|---|---|---|---|
| 442P | DYDMS (SEQ ID NO: 61) | SIYPDSGSTYYADSVQG (SEQ ID NO: 69) | DLHMGPEGPFDY (SEQ ID NO: 78) |
| 442S1 | DYDMS (SEQ ID NO: 61) | TIDLDSGSIYYADSVQG (SEQ ID NO: 70) | DLHMGPEGPFDY (SEQ ID NO: 78) |
| 442S2 | DYDMS (SEQ ID NO: 61) | SIYPDSGSTDYADSVQG (SEQ ID NO: 71) | DLHMGPEGPFDY (SEQ ID NO: 78) |
| 442S4 | DYDMS (SEQ ID NO: 61) | SIEPDFGSSYYADSVRG (SEQ ID NO: 72) | DLHMGPEGPFDY (SEQ ID NO: 78) |
| 442S5 | DYDMS (SEQ ID NO: 61) | IIEPDSGSIYYADSVQG (SEQ ID NO: 73) | DLHMGPEGPFDY (SEQ ID NO: 78) |
| 442S6 | DYDMS (SEQ ID NO: 61) | SIYPDSGSTDYADSVQG (SEQ ID NO: 71) | DRHMWPEGPFDY (SEQ ID NO: 79) |
| 442S9 | DYDMS (SEQ ID NO: 61) | SIYPDSGSTYYADSVQG (SEQ ID NO: 69) | DRHMWPEGPFDY (SEQ ID NO: 79) |
| 442S10 | DYDMS (SEQ ID NO: 61) | SIYPDSGSTYYADSVQG (SEQ ID NO: 69) | DRHMWPEGPFDY (SEQ ID NO: 79) |
| 442M3 | DYDMS (SEQ ID NO: 61) | SIYPDSGSTYYADSVQG (SEQ ID NO: 69) | DRHMWPEGPFDY (SEQ ID NO: 79) |
| 442M4 | DYDMS (SEQ ID NO: 61) | TIDLDSGSIYYADSVQG (SEQ ID NO: 70) | DLHMGPEGPFDY (SEQ ID NO: 78) |
| 442M5 | DYDMS (SEQ ID NO: 61) | TIDLDSGSIYYADSVQG (SEQ ID NO: 70) | DLHMGPEGPFDY (SEQ ID NO: 78) |
| 442M6 | DYDMS (SEQ ID NO: 61) | SIEPDSGSTDYADSVQG (SEQ ID NO: 74) | DRHMWPEGPFDY (SEQ ID NO: 79) |
| 442M7 | DYDMS (SEQ ID NO: 61) | TIEPDSGSTYYADSVQS (SEQ ID NO: 75) | DLHMGPEGPFDY (SEQ ID NO: 78) |
| 442M8 | DYDMS (SEQ ID NO: 61) | SIYPDSGSTYYADSVQG (SEQ ID NO: 69) | DLHMGPEGPFDY (SEQ ID NO: 78) |
| 442M10 | DYDMS (SEQ ID NO: 61) | SIYPDSGSTDYADSVQG (SEQ ID NO: 70) | DLHMWPEGPFDY (SEQ ID NO: 80) |
| 442M11 | DYDMS (SEQ ID NO: 61) | TIEPDYGSTLYADSVQG (SEQ ID NO: 75) | DLHMGPEGPFDY (SEQ ID NO: 78) |
| 472P | DYDMS (SEQ ID NO: 61) | GISYDGGNTYYADSVKG (SEQ ID NO: 76) | DPSWCLQDLCYYADGMDV (SEQ ID NO: 81) |
| 472S1 | WYDMT (SEQ ID NO: 62) | GISYDGGNTYYADSVKG (SEQ ID NO: 76) | DPSWCLQDLCYYADGMDV (SEQ ID NO: 81) |
| 472S2 | WYDLA (SEQ ID NO: 63) | GISYDGGNTYYADSVKG (SEQ ID NO: 76) | DPSWCLQDLCYYADGMDV (SEQ ID NO: 81) |
| 472S3 | WYDMS (SEQ ID NO: 64) | GISYDGGNTYYADSVKG (SEQ ID NO: 76) | DPSWCLQDLCYYADGMDV (SEQ ID NO: 81) |
| 472S4 | WYDIA (SEQ ID NO: 65) | GISYDGGNTYYADSVKG (SEQ ID NO: 76) | DPSWCLQDLCYYADGMDV (SEQ ID NO: 81) |
| 472M1 | WYDLS (SEQ ID NO: 66) | GISYDGGNTYYADSVKG (SEQ ID NO: 76) | DPSWCLQDLCYYADGMDV (SEQ ID NO: 81) |
| 451P | DYDMS (SEQ ID NO: 61) | AIYYDSGSIYYADSAKG (SEQ ID NO: 77) | DRLFVSDSTFDY (SEQ ID NO: 82) |
| 451M1 | DYDMS (SEQ ID NO: 61) | AIYYDSGSIYYADSAKG (SEQ ID NO: 77) | DRLFMSDSTFDY (SEQ ID NO: 83) |
| 451M2 | DYDMS (SEQ ID NO: 61) | AIYYDSGSIYYADSAKG (SEQ ID NO: 77) | DRLFASDSTFDY (SEQ ID NO: 84) |
| 451M3 | HYDMS (SEQ ID NO: 67) | AIYYDSGSIYYADSAKG (SEQ ID NO: 77) | DRLFASDSTFDY (SEQ ID NO: 84) |
| 451M4 | YYDMS (SEQ ID NO: 68) | AIYYDSGSIYYADSAKG (SEQ ID NO: 77) | DRLFASDSTFDY (SEQ ID NO: 84) |
| 451M5 | DYDMS (SEQ ID NO; 61) | AIYYDSGSIYYADSAKG (SEQ ID NO: 77) | DRLFESDSTFDY (SEQ ID NO: 85) |
| 451M6 | HYDMS (SEQ ID NO: 67) | AIYYDSGSIYYADSAKG (SEQ ID NO: 77) | DRLFESDSTFDY (SEQ ID NO: 85) |
| 451M7 | YYDMS (SEQ ID NO: 68) | AIYYDSGSIYYADSAKG (SEQ ID NO: 77) | DRLFESDSTFDY (SEQ ID NO: 85) |

TABLE 2

| Antibody | CDR-L1 | CDR-L2 | CDR-L3 |
|---|---|---|---|
| 442P | SGSSSNIGSNSVS (SEQ ID NO: 86) | SDNHRPS (SEQ ID NO: 88) | AAWDSSLSGYV (SEQ ID NO: 94) |
| 442S1 | SGSSSNIGSNSVS (SEQ ID NO: 86) | SDNHRPS (SEQ ID NO: 88) | QGWDTSLSGHV (SEQ ID NO: 95) |
| 442S2 | SGSSSNIGSNSVS (SEQ ID NO: 86) | SDNHRPS (SEQ ID NO: 88) | AAWDSSLSGYV (SEQ ID NO: 94) |
| 442S4 | SGSSSNIGSNSVS (SEQ ID NO: 86) | SDNHRPS (SEQ ID NO: 88) | AAWDSSLSGYV (SEQ ID NO: 94) |
| 442S5 | SGSSSNIGSNSVS (SEQ ID NO: 86) | SDNHRPS (SEQ ID NO: 88) | AAWDSSLSGYV (SEQ ID NO: 94) |
| 442S6 | SGSSSNIGSNSGS (SEQ ID NO: 87) | ADNWRPS (SEQ ID NO: 89) | AAWDSSLSGYV (SEQ ID NO: 94) |
| 442S9 | SGSSSNIGSNSGS (SEQ ID NO: 87) | ADNHRPS (SEQ ID NO: 90) | AAWDSSLSGYV (SEQ ID NO: 94) |
| 442S10 | SGSSSNIGSNSVS (SEQ ID NO: 86) | SDNHRPS (SEQ ID NO: 88) | AAWDSSLSGYV (SEQ ID NO: 94) |
| 442M3 | SGSSSNIGSNSGS (SEQ ID NO: 87) | ADNWRPS (SEQ ID NO: 89) | AAWDSSLSGYV (SEQ ID NO: 94) |
| 442M4 | SGSSSNIGSNSVS (SEQ ID NO: 86) | SDNHRPS (SEQ ID NO: 88) | VGWDSSLYGHV (SEQ ID NO: 96) |
| 442M5 | SGSSSNIGSNSVS (SEQ ID NO: 86) | SDNHRPS (SEQ ID NO: 88) | HAWDSSLWGDV (SEQ ID NO: 97) |
| 442M6 | SGSSSNIGSNSGS (SEQ ID NO: 87) | ADNWRPS (SEQ ID NO: 89) | AAWDSSLSGYV (SEQ ID NO: 94) |
| 442M7 | SGSSSNIGSNSVS (SEQ ID NO: 86) | SDNHRPS (SEQ ID NO: 88) | AAWDSSLSGYV (SEQ ID NO: 94) |
| 442M8 | SGSSSNIGSNSVS (SEQ ID NO: 86) | SDNHRPS (SEQ ID NO: 88) | HAWDSSLYVDV (SEQ ID NO: 98) |
| 442M10 | SGSSSNIGSNSVS (SEQ ID NO: 86) | ADNFRPS (SEQ ID NO: 91) | AAWDSSLSGYV (SEQ ID NO: 94) |
| 442M11 | SGSSSNIGSNSVS (SEQ ID NO: 86) | SDNHRPS (SEQ ID NO: 88) | HAWDSSLSGDF (SEQ ID NO: 99) |
| 472P | SGSSSNIGSNSVS (SEQ ID NO: 86) | ADSNRPS (SEQ ID NO: 92) | GSWDYSLSGYV (SEQ ID NO: 100) |
| 472S1 | SGSSSNIGSNSVS (SEQ ID NO: 86) | ADSNRPS (SEQ ID NO: 92) | GSWDYSLSGYV (SEQ ID NO: 100) |
| 472S2 | SGSSSNIGSNSVS (SEQ ID NO: 86) | ADSNRPS (SEQ ID NO: 92) | GSWDYSLSGYV (SEQ ID NO: 100) |
| 472S3 | SGSSSNIGSNSVS (SEQ ID NO: 86) | ADSNRPS (SEQ ID NO: 92) | GSWDYSLSGYV (SEQ ID NO: 100) |
| 472S4 | SGSSSNIGSNSVS (SEQ ID NO: 86) | ADSNRPS (SEQ ID NO: 92) | GSWDYSLSGYV (SEQ ID NO: 100) |
| 472M1 | SGSSSNIGSNSVS (SEQ ID NO: 86) | ADSNRPS (SEQ ID NO: 92) | GSWDYSLSGYV (SEQ ID NO: 100) |
| 451P | SGSPSNIGNNSVT (SEQ ID NO: 103) | YDSHRPS (SEQ ID NO: 93) | GSWDASLNGYV (SEQ ID NO: 101) |
| 451M1 | SGSPSNIGNNSVT (SEQ ID NO: 103) | YDSHRPS (SEQ ID NO: 93) | GSWDASLNGYV (SEQ ID NO: 101) |
| 451M2 | SGSPSNIGNNSVT (SEQ ID NO: 103) | YDSHRPS (SEQ ID NO: 93) | GSWDASLNGYV (SEQ ID NO: 101) |
| 451M3 | SGSPSNIGNNSVT (SEQ ID NO: 103) | YDSHRPS (SEQ ID NO: 93) | GSWDASLNGYV (SEQ ID NO: 101) |
| 451M4 | SGSPSNIGNNSVT (SEQ ID NO: 103) | YDSHRPS (SEQ ID NO: 93) | GSWDASLNGYV (SEQ ID NO: 101) |
| 451M5 | SGSPSNIGNNSVT (SEQ ID NO: 103) | YDSHRPS (SEQ ID NO: 93) | GSWDASLNGYV (SEQ ID NO: 101) |
| 451M6 | SGSPSNIGNNSVT (SEQ ID NO: 103) | YDSHRPS (SEQ ID NO: 93) | GSWDASLNGYV (SEQ ID NO: 101) |
| 451M7 | SGSPSNIGNNSVT (SEQ ID NO: 103) | YDSHRPS (SEQ ID NO: 93) | GSWDASLNGYV (SEQ ID NO: 101) |

Example 2. In-Vitro Effect of Anti-ErbB3 Antibody

1. Binding Affinity of Anti-ErbB3 Antibody to Human ErbB3 Protein

Binding affinities of the screened antibodies (Example 1.2) to ErbB3 protein (antigen) were measured.

In particular, the binding affinities of the anti-ErbB3 antibodies to the recombinant human ErbB3 protein (R&D systems) and the antigen-antibody interactive dynamics were measured using an Octet® QK384 system (Pall Life Sciences). After activation of carboxyl groups in 20 mM of 1-ethyl-3-(3-dimethylaminopropyl)carbodiimide hydrochloride (EDC) and 40 mM of N-hydroxysulfosuccinimide (sulfo-NHS) solution on an AR2G sensor (ForteBio), 10 μg/mL of human ErbB3 protein solution diluted with 10 mM of sodium acetate (pH 4.0) (ForteBio) was added to immobilize human ErbB3 protein onto the AR2G sensor. The AR2G sensor to which the human ErbB3 protein was immobilized was treated with 1 M of ethanolamine (ForteBio) to inactivate the remaining unreacted carboxyl groups. 12.5 nM, 25 nM, and 50 nM antibody solutions were each added onto the AR2G sensor and then the binding phase of the reaction product was observed for about 900 seconds. Next, a 1× kinetics buffer (ForteBio) was added to the reaction product, and the dissociation phase of the reaction product was observed for about 1200 seconds, followed by determination of an association constant (ka), a dissociation constant (kd), and an equilibrium dissociation constant (KD) of each type of antibody with Octet® analysis software (Pall Life® Sciences).

TABLE 3

| Antibody | KD (M) | ka (1/Ms) | kd (1/s) |
|---|---|---|---|
| 442P | 2.83E−10 | 1.25E+06 | 3.52E−04 |
| 442S1 | <1.0E−12 | 5.22E+05 | 3.94E−07 |
| 442S2 | 7.11E−11 | 1.17E+06 | 8.28E−05 |
| 442S4 | 3.71E−11 | 1.48E+06 | 5.47E−05 |
| 442S5 | 1.75E−11 | 1.57E+06 | 2.74E−05 |
| 442S6 | <1.0E−12 | 8.72E+05 | <1.0E−07 |
| 442S9 | 7.16E−11 | 8.21E+05 | 5.87E−05 |
| 442S10 | 1.14E−10 | 8.14E+05 | 9.29E−05 |
| 442M3 | 3.40E−12 | 7.71E+05 | 2.62E−06 |
| 442M4 | <1.0E−12 | 5.73E+05 | <1.0E−07 |
| 442M5 | <1.0E−12 | 6.65E+05 | <1.0E−07 |
| 442M6 | 2.01E−11 | 9.69E+05 | 1.95E−05 |
| 442M7 | 2.91E−11 | 1.56E+06 | 4.55E−05 |
| 442M8 | 2.56E−12 | 8.70E+05 | 2.23E−06 |
| 442M10 | <1.0E−12 | 4.71E+05 | <1.0E−07 |
| 442M11 | 5.43E−12 | 1.49E+06 | 8.09E−06 |
| 472P | 2.84E−10 | 1.79E+06 | 5.08E−04 |
| 472S1 | <1.0E−12 | 6.49E+05 | 3.33E−07 |
| 472S2 | <1.0E−12 | 1.07E+06 | <1.0E−07 |
| 472S3 | <1.0E−12 | 5.22E+05 | 1.43E−07 |
| 472S4 | 9.41E−12 | 1.15E+06 | 1.09E−05 |
| 472M1 | 1.25E−11 | 1.39E+06 | 1.74E−05 |
| 451P | 5.35E−11 | 1.18E+06 | 6.33E−05 |
| 451M1 | 2.48E−11 | 1.24E+06 | 3.08E−05 |
| 451M2 | 1.26E−11 | 1.24E+06 | 1.56E−05 |
| 451M3 | <1.0E−12 | 1.87E+06 | 2.30E−07 |
| 451M4 | 6.12E−12 | 2.01E+06 | 1.23E−05 |
| 451M5 | 2.17E−11 | 1.52E+06 | 3.29E−05 |
| 451M6 | 3.47E−12 | 1.20E+06 | 4.17E−06 |
| 451M7 | 4.92E−12 | 1.35E+06 | 6.63E−06 |

Referring to Table 3, the selected antibodies were found to have an equilibrium dissociation constant (KD) of about 0.1 nM to about 0.1 pM, indicating high binding affinities to the recombinant human ErbB3 protein.

2. ErbB3 Protein-HRG Binding Inhibitory Ability of Anti-ErbB3 Antibody

Whether the selected antibodies of Example 1.2 inhibit binding of ErbB3 protein and HRG as a ligand thereof was investigated.

In particular, a binding affinity of HRG (R&D systems) to human ErbB3 protein (R&D systems) was measured using an Octet® QK384 system (Pall Life Sciences). After 10 µg/mL of HRG protein was immobilized onto an AR2G sensor according to the same method as used in Example 2.1, the remaining unreacted carboxyl groups were inactivated using a 1M ethanolamine (ForteBio). Next, a mixed solution of 5 µg/mL of human ErbB3 protein (R&D systems) and 10 nM or 100 nM of anti-ErbB3 antibodies was added onto the AR2G sensor with the HRG protein immobilized thereon, and then the binding phase was observed for about 900 seconds. A reaction product to which no anti-ErbB3 antibodies were added was used as a negative control group. The amount of the remaining human ErbB3 protein bound to the HRG protein immobilized to the AR2G sensor was measured. A binding affinity (%) of ErbB3 protein and HRG in the presence of the anti-ErbB3 antibodies with respect to the negative control group was calculated. The results are shown in FIG. 2, in which the Y-axis represents a binding affinity (%) relative to the negative control group, and the X-axis represents antibodies at different concentrations of 0 nM, 10 nM, and 100 nM.

Referring to FIG. 2, the selected antibodies were found to inhibit binding of human ErbB3 protein and HRG protein, depending on the concentrations of the antibodies, whereas the HIgG control group showed no effect on the binding of ErbB3 and HRG.

3. ErbB2-ErbB3 Dimerization Inhibition Ability of Anti-ErbB3 Antibody

An investigation was carried out to assess the ability of the selected antibodies of Example 1. 2 to inhibit dimerization of ErbB2 protein and ErbB3 protein.

In particular, 100 µl of recombinant human ErbB2 protein (1 µg/mL) was applied to a multi-array 96-well plate (Thermo scientific) and incubated at 4□ for about 16 hours to coat the ErbB2 protein on the multi-array 96-well plate. 200 µl of 5% (w/v) BSA/PBS solution was applied to the coated plate and incubated at 37° C. for about 1 hour. A mixture of 50 µl of the recombinant human ErbB3 protein (0.6 µg/mL) and 50 µl of the selected anti-ErbB3 antibodies (0.2 µg/mL) was applied to the plate and the reaction mixture was incubated at 37° C. for about 2 hours. The resulting plate was washed three times with 0.05% (v/v) Tween/PBS solution. 100 µl of goat-anti-ErbB3 polyclonal antibody (1 µg/mL, R&D systems) was applied to the washed plate and incubated at 37° C. for about 1 hour. The plate was then washed three times with a 0.05% (v/v) Tween/PBS solution. 100 µl of anti-goat Fc-horseradish peroxidase (HRP) (Jackson Immunoresearch), diluted at 1:5000 with a 5% (w/v) BSA/PBS solution, was applied to the plate and then incubated at 37° C. for about 1 hour. The plate was then washed three times with a 0.05% (v/v) Tween/PBS solution. 100 µl of 3,3',5,5'-tetramethylbenzidine (TMB) as a substrate was applied to each well and incubated at room temperature for about 5 minutes, followed by terminating the reaction with 100 µl of a 2N sulfuric acid solution. A reaction mixture to which no anti-ErbB3 antibodies were added was used as a negative control group. The absorbance of the plate at a wavelength of 450 nm was measured. The binding affinities of ErbB2 protein and ErbB3 protein under the presence of anti-ErbB3 antibodies were calculated from the measured absorbance. Human IgG, which does not bind to ErbB3, was used as another negative control group.

The binding affinities (%) of ErbB2 protein and ErbB3 protein in the presence of anti-ErbB3 antibodies with respect to the negative control group were calculated. The results are shown in FIG. 3, wherein the Y-axis denotes a binding affinity (%) relative to the negative control group, and HIgG denotes human IgG.

Referring to FIG. 3, the selected antibodies were found to inhibit the dimerization of ErbB2 protein and ErbB3 protein, whereas the HIgG control group did not demonstrate any inhibition of dimerization.

4. ErbB3 and Akt Phosphorylation Inhibition Ability of Anti-ErbB3 Antibody

An investigation was carried out to assess the ability of the selected antibodies of Example 1. 2 to inhibit phosphorylation of ErbB3 protein and Akt.

In particular, about $5 \times 10^5$ MCF7 breast cancer cells (from the National Institutes of Health) were inoculated onto a 24-well plate, and Roswell Park Memorial Institute (RPMI)-1640 medium (Invitrogen) including penicillin-streptomycin antibiotic (Invitrogen) and 10% (v/v) of fetal bovine serum (FBS) was added to the cells on the 24-well plate and incubated at 37° C. under 5% $CO_2$ conditions for about 24 hours. Next, the medium was exchanged with fresh RPMI-1640 medium, and the cells were cultured under serum starving conditions for about 24 hours. Next, the selected anti-ErbB3 antibodies were added to the cells and incubated at 37° C. under 5% $CO_2$ conditions for about 2 hours. The antibodies 442P and 472P were each added to the cells at concentrations of about 67 nM, 13 nM, 3 nM, 534 pM, 107 pM, 21 pM, and 4 pM, while the antibodies 442S1, 442S5, 442M6, 472S2, and 472M1 were added to the cells at concentrations of 13 nM, 3 nM, 834 pM, 208 pM, 52 pM, and 13 pM. After 1 hours and 45 minutes, HRG was added to the cells and incubated at 37° C. under 5% $CO_2$ conditions for about 15 minutes to stimulate the cells (total antibody treatment time: 2 hours). The cells were washed with cooled PBS and Cell Lysis Solution (Cell Signaling Technology) was added to thereby collect the cells. After quantification of protein in the selected cells was performed by BCA assay, phosphorylation levels of ErbB3 or Akt were analyzed.

The phosphorylation level of ErbB3 was assayed using a Phospho-ErbB3 Detection Kit (Cell Signaling Technology). After binding the cell protein to an ErbB3 antibody-coated ELISA plate, phosphotyrosine mouse detection antibody and HRP-conjugated anti-mouse antibody were developed on the ELISA plate. Next, tetramethylbenzidine (TMB) substrate was added to the reaction product, the reaction was stopped with reaction stop solution of the kit, and absorbance was measured with a plate reader.

The phosphorylation level of Akt1 was assayed using a Phospho-Akt1 Detection Kit (Cell Signaling Technology). After binding the cell protein to an anti-phosphoserine-coated ELISA plate, Akt1-specific detection antibody and HRP-conjugated antibody were developed on the ELISA plate. Next, after reaction with TMB substrate, the reaction was stopped with Reaction Stop Solution of the kit, and absorbance was measured with a plate reader.

FIGS. 4A and 4B are graphs of ErbB3 and Akt phosphorylation ratios, respectively, with respect to antibody concentration, plotted based on the measured absorbance. The half maximal inhibitory concentrations ($IC_{50}$) of the antibodies were calculated. The results are shown in Table 4.

TABLE 4

| Assay | Antibody | $IC_{50}$ (nM) |
|---|---|---|
| Inhibition of ErbB3 phosphorylation | 442P | 1.046 |
| | 472P | 1.451 |
| | 442S1 | 0.2221 |
| | 442S5 | 0.08537 |
| | 442M6 | 0.271 |
| | 472S2 | 0.1478 |
| | 472M1 | 0.2761 |
| Inhibition of Akt phosphorylation | 442S1 | 0.2393 |
| | 442S5 | 0.1674 |
| | 442M6 | 0.3041 |
| | 472S2 | 0.1953 |
| | 472M1 | 0.2463 |

Referring to FIGS. 4A and 4B and Table 4, the selected antibodies were found to inhibit phosphorylation of ErbB3 and Akt.

Similarly, it was also found that the selected antibodies inhibit phosphorylation of ErbB3 and Akt in breast cancer cell lines MDA-MB-468 and BT474, skin cancer cell line A431, pancreatic cancer cell line BxPC3, head and neck cancer cell line FaDu, lung cancer cell line A549, colorectal cancer cell line LoVo, melanoma cell line MALME-3M, ovarian cancer cell line OVCAR-8, and prostate cancer cell line DU145.

5. Pancreatic Cancer Cell Line BxPC3 Proliferation Inhibition Ability of Anti-ErbB3 Antibody An investigation was carried out to assess the ability of the selected antibodies of Example 1.2 to inhibit proliferation of BxPC3 pancreatic cancer cells.

In particular, about $1 \times 10^4$ BxPC3 pancreatic cancer cells (American Type Culture Collection) were inoculated onto a 96-well plate, and RPMI-1640 medium (Invitrogen) including 10% FBS was added to the cells on the 96-well plate and incubated at 37° C. under 5% $CO_2$ conditions for about 24 hours. Next, the medium was exchanged with an RPMI-1640 medium including 0.1% (v/v) FBS. 0.02 μg/mL, 0.2 μg/mL, 2 μg/mL, and 20 μg/mL of the 442S1 antibody or 442M6 antibody were added to the incubated cells and cultured at 37° C. under 5% $CO_2$ conditions for about 2 hours. 50 ng/mL of HRG was further added to the cultured cells and incubated at 37° C. under 5% $CO_2$ conditions for about 120 hours. Cultured cells without added antibodies were used as a negative control group. The number of viable cells was measured using a CellTiter-Glo Luminescent Cell Viability Assay (Promega). The relative proliferation rates were calculated based on the measured results. The results are shown in FIG. 5.

Referring to FIG. 5, the selected antibodies were found to inhibit proliferation of BxPC3 pancreatic cancer cells in a concentration-dependent manner.

Example 3. In-Vivo Effect of Anti-ErbB3 Antibody

1. Tumor Growth Inhibition Using BT474 Breast Cancer Xenograft Model

An investigation was carried to assess the ability of the selected antibodies of Example 1.2 to inhibit growth of tumors in a breast cancer cell xenograft animal model.

In particular, human breast cancer BT474 cells (American Type Culture Collection) were cultured in Dulbecco's Modified Eagle's medium (DMEM) medium (Hyclone) including 10% FBS. 17 β-estradiol-sustained release pellets (0.36 mg/60 days, Innovative Research of America) were subcutaneously inoculated into female NOD/SCID mice (HFK Bio-Technology Co. Ltd.) one day before the inoculation of cancer cells to maintain blood estrogen level. About $1 \times 10^7$ of BT474 cancer cells were suspended in 100 μl of PBS containing 50% Matrigel, and the suspended cancer cells were injected into the fat tissue under a nipple of each mouse. Weights of the mice were measured twice a week, and the tumor volume was calculated using the equation of "$0.5 \, a \times b^2$", where a and b were the long and short diameters of the tumor, respectively. When the tumor volume reached about 210 $mm^3$ after 7 days from the inoculation of the cancer cells, the mice were randomly assigned to 7 groups, each including 10 mice. PBS (negative control group), antibodies 442P, 442S1, 442S5, 442M6, 472S2, and 472M1 were administered into the tail veins of the mice in each group twice a week at a dose of 10 mg/kg of body weight for 4 weeks. After the inoculation of the cancer cells, the tumor volume after the administration of the antibodies was calculated. The results are shown in FIG. 6.

Referring to FIG. 6, it was found that the tumor volume was reduced by the administration of the antibodies relative to the negative control group, and the selected antibodies inhibited tumor growth.

2. Tumor Growth Inhibition Using MDA-MB-468 Breast Cancer Xenograft Model

Human breast cancer cells MDA-MB-468 (American Type Culture Collection) were incubated in an L-15 medium (Hyclone) including 10% (v/v) of fetal bovine serum. About $5 \times 10^6$ cancer cells were suspended in 100 μL of PBS including 50% Matrigel and subcutaneously injected into the flank region of female Nu/Nu mice (Vital River laboratories, Ltd). Weights of the mice were measured twice a week, and a tumor volume was calculated using the equation of "0.5 a×b², where a and b were the long and short diameters of the tumor, respectively. When the tumor volume reached about 210 mm³ after 7 days from the injection of the cancer cells, the mice were randomly assigned to 7 groups, each including 10 mice. PBS (negative control group), antibodies 442P, 442S1, 442S5, 442M6, 472S2, and 472M1 were administered into the tail veins of the mice in each group twice a week at a dose of 10 mg/kg of body weight for 4 weeks. After the inoculation of the cancer cells, the tumor volume after the administration of the antibodies was calculated. The results are shown in FIG. 7.

Referring to FIG. 7, it was found that the tumor volume was reduced by the administration of the antibodies relative to the negative control group, and the selected antibodies inhibited tumor growth.

3. Tumor Growth Inhibition Using A431 Skin Cancer Xenograft Model

Human skin cancer A431 cells (American Type Culture Collection) were incubated in DMEM medium (Hyclone) including 10% FBS. About 5×10⁶ cancer cells were suspended in 100 μl of PBS including 50% of Matrigel and subcutaneously injected into the flank region of female Balb/c nude mice (HFK Bio-Technology Co. Ltd.). Weights of the mice were measured twice a week, and a tumor volume was calculated using the equation of "0.5 a×b²", where a and b were the long and short diameters of the tumor, respectively. When the tumor volume reached about 160 mm³ after 7 days from the inoculation of the cancer cells, the mice were randomly assigned to 7 groups, each including 10 mice. PBS (negative control group), antibodies 442P, 442S1, 442S5, 442M6, 472S2, and 472M1 were administered into the tail veins of the mice in each group twice a week at a dose of 10 mg/kg of body weight for 4 weeks. After the inoculation of the cancer cells, the tumor volume after the administration of the antibodies was calculated. The results are shown in FIG. 8.

Referring to FIG. 8, it was found that the tumor volume was reduced by the administration of the antibodies relative to the negative control group, and the selected antibodies inhibited tumor growth.

4. Tumor Growth Inhibition Using Tumor Xenograft Model

The antibody 442S1 was administered into FaDu head and neck cancer, pancreatic cancer, or lung cancer animal model, and the antibodies 442P or 472P antibodies were administered into gastric cancer animal model, in the same manner as described in Examples 3.1 to 3.3. As a result, it was found that the tumor volume was reduced by the administration of the antibodies relative to the negative control group, and the selected antibodies inhibited tumor growth.

Example 4. Effect of Combined Administration of Anti-Cancer Drug and Anti-ErbB3 Antibody An investigation was carried out to assess the ability of combined use of the antibodies 442S1 and Cetuximab to improve anti-cancer effects in FaDu head and neck cancer model.

Human head and neck cancer FaDu cells (Shanghai Institutes for Biological Sciences) were incubated in EMEM medium (Hyclone) including 10% FBS. About 5×10⁶ cancer cells were suspended in 100 μl of PBS including 50% Matrigel and subcutaneously injected into the flank region of the female NOD/SCID mice (HFK Bio-Technology Co. Ltd). Weights of the mice were measured twice a week, and a tumor volume was calculated using the equation of "0.5 a×b²", where a and b were the long and short diameters of the tumor, respectively. When the tumor volume reached about 150 mm³ after 7 days from the inoculation of the cancer cells, the mice were randomly assigned to 4 groups, each including 10 mice. PBS (negative control group), antibodies 442S1 and Cetuximab (Merck) were administered into the tail veins of the mice in each group twice a week at a dose of 5 mg/kg of body weight for 4 weeks. In a combined use treatment group, antibodies 442S1 and Cetuximab were administered into the tail veins of the mice twice a week at a dose of 5 mg/kg of body weight for 4 weeks. Then, no antibodies were administered for one week. The tumor sizes were measured twice a week. The volume of the tumors after the administration of the antibodies or the combined administration was calculated. The results are shown in FIG. 9, in which down arrows (↓) denote time injecting cancer cells, and *** denotes results of Tukey's multiple comparison test after one-way ANOVA ($p<0.001$).

Referring to FIG. 9, in the combined use of antibodies 442S1 and Cetuximab treatment group, the tumor volume was reduced from the initial administration stage and was about 68 mm³ on average at the end of the test (n=10/group). Accordingly, the combined administration of the selected antibody and Cetuximab was found to improve anti-cancer efficacy.

Example 5. Anti-Cancer Drug Resistance Improvement Effect of Anti-ErbB3 Antibody 1. Paclitaxel Resistance Improvement Effect in Breast Cancer Apoptotic effects of Paclitaxel in breast cancer cell line ZR-75-30 may be reduced in the presence of HRG due to the activation of an ErbB3 signal transduction pathway (Wang S et al., Oncogene, 29, 4225-4236, 2010). An investigation was carried out to assess the ability of the screened antibodies to improve resistance to Paclitaxel used as an anti-cancer drug and impart an anti-cancer effect.

About 1×10⁴ ZR-75-30 cells (American Type Culture Collection) were inoculated onto a plate and incubated in RPMI 1640 medium (Invitrogen) including 10% (v/v) FBS at 37° C. under 5% $CO_2$ conditions for about 24 hours. The medium was then exchanged with fresh medium (100 ng/mL HRG added) including 0.1% (v/v) FBS, and further incubation was performed at 37° C. under 5% $CO_2$ conditions for about 24 hours. 10 nM of Paclitaxel (Bristol-Myers Squibb) and 25 μg/mL of antibody 442S1 were added to the cultured cells and incubated at 37° C. under 5% $CO_2$ conditions for about 72 hours. The cultured cells were collected, and the activity of caspase 3/7 as an apoptotic marker was measured using a Caspase 3/7 Substrate Assay (Promega). The measured activity of caspase 3/7 is shown in FIG. 10, in which RLU denotes relative luminescence units, and ** denotes t-test results ($p<0.01$).

Referring to FIG. 10, the activity of caspase 3/7 was reduced by Paclitaxel, but was improved by the combined treatment of Paclitaxel and antibody 442S1, compared with the treatment with Paclitaxel alone (n=3). Accordingly, it was found that the apoptotic effect of Paclitaxel may be reduced in the presence of HRG, but recovered by administration of antibody 442S1.

2. Cetuximab Resistance Improvement Effect in Colorectal Cancer

Cetuximab is effective in suppressing cancer cell proliferation in DiFi colorectal cancer cells, but loses its efficacy in the presence of HRG due to the activation of an ErbB3 signal transduction pathway. An investigation was carried out to assess the ability of the screened antibodies to overcome resistance to Cetuximab and impart cancer cell proliferation suppression effects.

In particular, DiFi colon cancer cells were incubated in RPMI-1640 medium (Invitrogen) including an antibiotic (Penicillin-Streptomycin, Invitrogen) and 10% FBS. About $1\times10^4$ DiFi cells were inoculated onto a 96-well plate and incubated at 37° C. under 5% $CO_2$ conditions for about 24 hours. Cetuximab and anti-ErbB3 antibody were mixed together in equal concentrations of 200 μg/mL to obtain an Cetuximab/anti-ErbB3 antibody solution, which was then mixed with an equal amount of HRG (40 ng/mL). The Cetuximab/anti-ErbB3 antibody/HRG solution was applied to a 96-well plate and incubated at 37° C. under 5% $CO_2$ conditions for about 72 hours. Cells cultured without antibodies and HRG were used as a negative control group. The number of viable cells was measured using a CellTiter-Glo luminescent cell viability assay (Promega). Cell proliferation rates were calculated based on the measured results. The results are shown in FIG. 11, in which *** denotes t-test results ($p<0.001$).

Referring to FIG. 11, the cell proliferation suppression effect of Cetuximab was reduced in the presence of HRG, but recovered in the treatment group which received Cetuximab and 442S1 antibodies in combination. Accordingly, it was found that the cell proliferation suppression effect of Cetuximab may be reduced in the presence of HRG, i.e., an ErbB3 ligand, but may be recovered by 442S1 antibodies blocking the HRG-ErbB3 signaling pathway.

3. Improvement in Resistance to Cetuximab in Cetuximab Resistant Xenograft Model FaDu human head and neck cancer cells (Shanghai Institutes of Biological Sciences) were incubated in EMEM medium (Hyclone) including 10% FBS (Invitrogen), 0.01 mM NEAA (Non-Essential Amino Acid, Hyclone), and 2 mM L-glutamine (Invitrogen). About $5\times10^6$ FaDu cancer cells were suspended in 100 μl of PBS and then subcutaneously injected into the frank region of the female NOD SCID mice (HFK Bio-Technology Co., Ltd.). Weights of the mice were measured twice a week, and tumor volume was calculated using the equation of "$0.5\ a\times b^2$", where a and b were the long and short diameters of the tumor, respectively. When the tumor volume reached about 165 $mm^3$ after 8 days from the inoculation of the cancer cells, the mice were randomly selected. PBS (negative control group) or Cetuximab was administered into the tail veins of the mice in each group twice a week at a dose of 5 mg/kg of weight for 6.5 weeks. When the tumor growth suppression effect of Cetuximab was not maintained such that tumor volume increased to about 840 me, ten mice were randomly selected from each group, and 5 mg/kg of Cetuximab, 10 mg/kg of antibody 442S1 or combination of 5 mg/kg of Cetuximab and 10 mg/kg of antibody 442S1 was administered to the mice twice a week for 2 weeks. Tumor volumes were measured twice a week. The results are shown in FIG. 12.

Referring to FIG. 12, it was found that a significant tumor suppression effect was observed in the treatment group that received antibody 442S1 alone or antibody 442S1 and Cetuximab in combination, compared with the treatment group that received Cetuximab alone, indicating that antibody 442S1 may overcome resistance to Cetuximab and suppress tumor growth.

It should be understood that example embodiments described herein should be considered in a descriptive sense only and not for purposes of limitation. Descriptions of features or aspects within each example embodiment should typically be considered as available for other similar features or aspects in other embodiments.

While one or more example embodiments have been described with reference to the figures, it will be understood by those of ordinary skill in the art that various changes in form and details may be made therein without departing from the spirit and scope of the inventive concept as defined by the following claims.

---

The invention claimed is:

1. An antibody or an antigen-binding fragment thereof that specifically binds to ErbB3, comprising:
heavy chain complementarity determining regions (CDR-Hs) and light chain complementarity determining regions (CDR-Ls), wherein the antibody is selected from the group consisting of:

(1) an antibody comprising a CDR-H1 having the sequence of SEQ ID NO: 61, a CDR-H2 having the sequence of SEQ ID NO: 69, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 94;

(2) an antibody comprising a CDR-H1 having the sequence of SEQ ID NO: 61, a CDR-H2 having the sequence of SEQ ID NO: 70, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 95;

(3) an antibody comprising a CDR-H1 having the sequence of SEQ ID NO: 61, a CDR-H2 having the sequence of SEQ ID NO: 71, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 94;

(4) an antibody comprising a CDR-H1 having the sequence of SEQ ID NO: 61, a CDR-H2 having the sequence of SEQ ID NO: 72, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 94;

(5) an antibody comprising a CDR-H1 having the sequence of SEQ ID NO: 61, a CDR-H2 having the sequence of SEQ ID NO: 73, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 94;

(6) an antibody comprising a CDR-H1 having the sequence of SEQ ID NO: 61, a CDR-H2 having the sequence of SEQ ID NO: 71, a CDR-H3 having the sequence of SEQ ID NO: 79, a CDR-L1 having the sequence of SEQ ID NO: 87, a CDR-L2 having the sequence of SEQ ID NO: 89, and a CDR-L3 having the sequence of SEQ ID NO: 94;

(7) an antibody comprising a CDR-H1 having the sequence of SEQ ID NO: 61, a CDR-H2 having the sequence of SEQ ID NO: 69, a CDR-H3 having the sequence of SEQ ID NO: 79, a CDR-L1 having the sequence of SEQ ID NO: 87, a CDR-L2 having the sequence of SEQ ID NO: 90, and a CDR-L3 having the sequence of SEQ ID NO: 94;

(8) an antibody comprising a CDR-H1 having the sequence of SEQ ID NO: 61, a CDR-H2 having the sequence of SEQ ID NO: 69, a CDR-H3 having the sequence of SEQ ID NO: 79, a CDR-L1 having the sequence of SEQ ID NO: 86, a CDR-L2 having the sequence of SEQ ID NO: 88, and a CDR-L3 having the sequence of SEQ ID NO: 94;

(9) an antibody comprising a CDR-H1 having the sequence of SEQ ID NO: 61, a CDR-H2 having the sequence of SEQ ID NO: 69, a CDR-H3 having the sequence of SEQ ID NO: 79, a CDR-L1 having the sequence of SEQ ID NO: 87, a CDR-L2 having the sequence of SEQ ID NO: 89, and a CDR-L3 having the sequence of SEQ ID NO: 94;

(10) an antibody comprising a CDR-H1 having the sequence of SEQ ID NO: 61, a CDR-H2 having the sequence of SEQ ID NO: 70, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 96;

(11) an antibody comprising a CDR-H1 having the sequence of SEQ ID NO: 61, a CDR-H2 having the sequence of SEQ ID NO: 70, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 97;

(12) an antibody comprising a CDR-H1 having the sequence of SEQ ID NO: 61, a CDR-H2 having the sequence of SEQ ID NO: 74, a CDR-H3 having the sequence of SEQ ID NO: 79, a CDR-L1 having the sequence of SEQ ID NO: 87, a CDR-L2 having the sequence of SEQ ID NO: 89, and a CDR-L3 having the sequence of SEQ ID NO: 94;

(13) an antibody comprising a CDR-H1 having the sequence of SEQ ID NO: 61, a CDR-H2 having the sequence of SEQ ID NO: 75, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 94;

(14) an antibody comprising a CDR-H1 having the sequence of SEQ ID NO: 61, a CDR-H2 having the sequence of SEQ ID NO: 69, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 98;

(15) an antibody comprising a CDR-H1 having the sequence of SEQ ID NO: 61, a CDR-H2 having the sequence of SEQ ID NO: 71, a CDR-H3 having the sequence of SEQ ID NO: 80, a CDR-L1 having the sequence of SEQ ID NO: 86, a CDR-L2 having the sequence of SEQ ID NO: 91, and a CDR-L3 having the sequence of SEQ ID NO: 94;

(16) an antibody comprising a CDR-H1 having the sequence of SEQ ID NO: 61, a CDR-H2 having the sequence of SEQ ID NO: 102, a CDR-H3 having the sequence of SEQ ID NO: 78, a CDR-L1 having the sequence of SEQ ID NO: 86, a CDR-L2 having the sequence of SEQ ID NO: 88, and a CDR-L3 having the sequence of SEQ ID NO: 99;

(17) an antibody comprising a CDR-H1 having the sequence of SEQ ID NO: 61, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(18) an antibody comprising a CDR-H1 having the sequence of SEQ ID NO: 62, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(19) an antibody comprising a CDR-H1 having the sequence of SEQ ID NO: 63, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(20) an antibody comprising a CDR-H1 having the sequence of SEQ ID NO: 64, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(21) an antibody comprising a CDR-H1 having the sequence of SEQ ID NO: 65, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(22) an antibody comprising a CDR-H1 having the sequence of SEQ ID NO: 66, a CDR-H2 having the sequence of SEQ ID NO: 76, a CDR-H3 having the sequence of SEQ ID NO: 81, a CDR-L1 having the sequence of SEQ ID NO: 86, a CDR-L2 having the sequence of SEQ ID NO: 92, and a CDR-L3 having the sequence of SEQ ID NO: 100;

(23) an antibody comprising a CDR-H1 having the sequence of SEQ ID NO: 61, a CDR-H2 having the sequence of SEQ ID NO: 77, a CDR-H3 having the sequence of SEQ ID NO: 82, a CDR-L1 having the sequence of SEQ ID NO: 103, a CDR-L2 having the sequence of SEQ ID NO: 93, and a CDR-L3 having the sequence of SEQ ID NO: 101;

(24) an antibody comprising a CDR-H1 having the sequence of SEQ ID NO: 61, a CDR-H2 having the sequence of SEQ ID NO: 77, a CDR-H3 having the sequence of SEQ ID NO: 83, a CDR-L1 having the sequence of SEQ ID NO: 103, a CDR-L2 having the sequence of SEQ ID NO: 93, and a CDR-L3 having the sequence of SEQ ID NO: 101;

(25) an antibody comprising a CDR-H1 having the sequence of SEQ ID NO: 61, a CDR-H2 having the sequence of SEQ ID NO: 77, a CDR-H3 having the sequence of SEQ ID NO: 84, a CDR-L1 having the sequence of SEQ ID NO: 103, a CDR-L2 having the sequence of SEQ ID NO: 93, and a CDR-L3 having the sequence of SEQ ID NO: 101;

(26) an antibody comprising a CDR-H1 having the sequence of SEQ ID NO: 67, a CDR-H2 having the sequence of SEQ ID NO: 77, a CDR-H3 having the sequence of SEQ ID NO: 84, a CDR-L1 having the sequence of SEQ ID NO: 103, a CDR-L2 having the sequence of SEQ ID NO: 93, and a CDR-L3 having the sequence of SEQ ID NO: 101;

(27) an antibody comprising a CDR-H1 having the sequence of SEQ ID NO: 68, a CDR-H2 having the sequence of SEQ ID NO: 77, a CDR-H3 having the sequence of SEQ ID NO: 84, a CDR-L1 having the sequence of SEQ ID NO: 103, a CDR-L2 having the sequence of SEQ ID NO: 93, and a CDR-L3 having the sequence of SEQ ID NO: 101,

(28) an antibody comprising a CDR-H1 having the sequence of SEQ ID NO: 61, a CDR-H2 having the sequence of SEQ ID NO: 77, a CDR-H3 having the sequence of SEQ ID NO: 85, a CDR-L1 having the sequence of SEQ ID NO: 103, a CDR-L2 having the sequence of SEQ ID NO: 93, and a CDR-L3 having the sequence of SEQ ID NO: 101,

(29) an antibody comprising a CDR-H1 having the sequence of SEQ ID NO: 67, a CDR-H2 having the sequence of SEQ ID NO: 77, a CDR-H3 having the sequence of SEQ ID NO: 85, a CDR-L1 having the sequence of SEQ ID NO: 103, a CDR-L2 having the sequence of SEQ ID NO: 93, and a CDR-L3 having the sequence of SEQ ID NO: 101, and

(30) an antibody comprising a CDR-H1 having the sequence of SEQ ID NO: 68, a CDR-H2 having the sequence of SEQ ID NO: 77, a CDR-H3 having the sequence of SEQ ID NO: 85, a CDR-L1 having the sequence of SEQ ID NO: 103, a CDR-L2 having the sequence of SEQ ID NO: 93, and a CDR-L3 having the sequence of SEQ ID NO: 101.

2. The antibody or the antigen-binding fragment of claim 1, wherein the heavy chain variable region further comprises an amino acid sequence selected from the group consisting of SEQ ID NOs: 1 to 30.

3. The antibody or the antigen-binding fragment of claim 1, wherein the light chain variable region further comprises an amino acid sequence selected from the group consisting of SEQ ID NOs: 31 to 60.

4. The antibody or the antigen-binding fragment of claim 1, wherein the antibody or the antigen-binding fragment inhibits (a) binding of ErbB3 protein to a material specifically binding thereto, (b) dimerization of ErbB1 protein and ErbB3 protein, (c) dimerization of ErbB2 protein and ErbB3 protein, (d) phosphorylation of ErbB3 or Akt, or (e) a combination thereof.

5. The antibody or the antigen-binding fragment of claim 4, wherein the material specifically binding to the ErbB3 protein is heregulin (HRG).

6. The antibody or the antigen-binding fragment of claim 1,
wherein the antibody is IgA, IgD, IgE, IgG, or IgM; or
wherein the antigen-binding fragment is scFv, (scFv)2, Fv, Fab, Fab', F(ab')2, or a combination thereof; or
wherein the antibody or the antigen-binding fragment thereof is modified by conjugation or binding, glycosylation, tag attachment, or a combination thereof.

7. A pharmaceutical composition for treatment of a disease related to activation or overexpression of ErbB3 protein, the pharmaceutical composition comprising the antibody or the antigen-binding fragment of claim 1.

8. The pharmaceutical composition of claim 7, wherein the disease related to activation or overexpression of the ErbB3 protein is cancer.

9. The pharmaceutical composition of claim 8, wherein the cancer is selected from the group consisting of breast cancer, skin cancer, head and neck cancer, pancreatic cancer, lung cancer, colon cancer, colorectal cancer, gastric cancer, ovarian cancer, prostate cancer, bladder cancer, uterine cancer, liver cancer, kidney cancer, clear cell sarcoma, melanoma, cerebrospinal tumors, brain cancer, thymoma, mesothelioma, esophageal cancer, biliary tract cancer, testicular cancer, germinal cancer, thyroid cancer, parathyroid cancer, cervical cancer, endometrial cancer, lymphoma, myelodysplastic syndromes (MDS), myelofibrosis, acute leukemia, chronic leukemia, multiple myeloma, Hodgkin's disease, endocrine cancer, and sarcoma.

10. The pharmaceutical composition of claim 7, further comprising an anti-cancer drug.

11. The pharmaceutical composition of claim 10, wherein the anti-cancer drug is Cetuximab, Panitumumab, Erlotinib, Gefitinib, Trastuzumab, T-DM1, Pertuzumab, Lapatinib, Paclitaxel, Tamoxifen, Cisplatin, anti-CTLA-4 antibody, anti-PD-1 antibody, anti-PD-L1 antibody, 5-fluorouracil (5FU), Gemcitabine, or a combination thereof.

12. The pharmaceutical composition of claim 10, wherein the pharmaceutical composition further comprises a single composition or separate compositions.

13. A method of treatment of a disease related to activation or overexpression of ErbB3 protein in an individual, the method comprising administering the antibody or the antigen-binding fragment of claim 1 to the individual.

14. The method of claim 13, further comprising administering an anti-cancer drug to the individual.

15. The method of claim 14, wherein the anti-cancer drug is administered at the same time with, separately from, or sequentially with the antibody or the antigen-binding fragment of claim 1.

16. The method of claim 14, wherein the antibody, the antigen-binding fragment thereof, the anti-cancer drug, or a combination thereof are administered to the individual by oral, intravenous, intramuscular, transdermal, mucosal, intranasal, intratracheal, subcutaneous administration and a combination thereof.

17. The method of claim 14, wherein the antibody, the antigen-binding fragment thereof, the anti-cancer drug, or a combination thereof are administered systemically or locally.

18. A method of treatment of cancer drug resistance in an individual, the method comprising administering the antibody or the antigen-binding fragment of claim 1 to the individual.

19. A pharmaceutical composition for treatment of a disease related to activation or overexpression of ErbB3 protein, the pharmaceutical composition comprising the antibody or the antigen-binding fragment of claim 2.

20. A pharmaceutical composition for treatment of a disease related to activation or overexpression of ErbB3 protein, the pharmaceutical composition comprising the antibody or the antigen-binding fragment of claim 3.

21. A pharmaceutical composition for treatment of a disease related to activation or overexpression of ErbB3 protein, the pharmaceutical composition comprising the antibody or the antigen-binding fragment of claim 4.

22. A pharmaceutical composition for treatment of a disease related to activation or overexpression of ErbB3 protein, the pharmaceutical composition comprising the antibody or the antigen-binding fragment of claim 5.

23. A pharmaceutical composition for treatment of a disease related to activation or overexpression of ErbB3 protein, the pharmaceutical composition comprising the antibody or the antigen-binding fragment of claim 6.

24. A method of treatment of a disease related to activation or overexpression of ErbB3 protein in an individual, the method comprising administering the antibody or the antigen-binding fragment of claim 2 to the individual.

25. A method of treatment of a disease related to activation or overexpression of ErbB3 protein in an individual, the method comprising administering the antibody or the antigen-binding fragment of claim 3 to the individual.

26. A method of treatment of a disease related to activation or overexpression of ErbB3 protein in an individual, the method comprising administering the antibody or the antigen-binding fragment of claim 4 to the individual.

27. A method of treatment of a disease related to activation or overexpression of ErbB3 protein in an individual, the method comprising administering the antibody or the antigen-binding fragment of claim 5 to the individual.

28. A method of treatment of a disease related to activation or overexpression of ErbB3 protein in an individual, the method comprising administering the antibody or the antigen-binding fragment of claim 6 to the individual.

29. A method treatment of cancer drug resistance in an individual, the method comprising administering the antibody or the antigen-binding fragment of claim 2 to the individual.

30. A method treatment of cancer drug resistance in an individual, the method comprising administering the antibody or the antigen-binding fragment of claim 3 to the individual.

31. A method treatment of cancer drug resistance in an individual, the method comprising administering the antibody or the antigen-binding fragment of claim 4 to the individual.

32. A method of treatment of cancer drug resistance in an individual, the method comprising administering the antibody or the antigen-binding fragment of claim 5 to the individual.

33. A method of treatment of cancer drug resistance in an individual, the method comprising administering the antibody or the antigen-binding fragment of claim 6 to the individual.

* * * * *